United States Patent
Sama

(10) Patent No.: US 12,420,091 B2
(45) Date of Patent: Sep. 23, 2025

(54) ORAL MUSCLE TRAINING

(71) Applicant: Signifier Medical Technologies Limited, Leicester (GB)

(72) Inventor: Anshul Sama, Nottingham (GB)

(73) Assignee: Signifier Medical Technologies Limited, London (GB)

( * ) Notice: Subject to any disclaimer, the term of this patent is extended or adjusted under 35 U.S.C. 154(b) by 0 days.

(21) Appl. No.: 16/655,419

(22) Filed: Oct. 17, 2019

(65) Prior Publication Data

US 2020/0121924 A1    Apr. 23, 2020

(30) Foreign Application Priority Data

Oct. 17, 2018  (GB) ..................................... 1816882
Oct. 22, 2018  (GB) ..................................... 1817164

(51) Int. Cl.

| | |
|---|---|
| *A61N 1/36* | (2006.01) |
| *A61B 5/00* | (2006.01) |
| *A61B 5/03* | (2006.01) |
| *A61B 5/053* | (2021.01) |
| *A61B 5/0538* | (2021.01) |
| *A61B 7/00* | (2006.01) |
| *A61N 1/05* | (2006.01) |
| *A63B 23/03* | (2006.01) |

(Continued)

(52) U.S. Cl.
CPC .......... *A61N 1/3601* (2013.01); *A61B 5/0088* (2013.01); *A61B 5/038* (2013.01); *A61B 5/0538* (2013.01); *A61B 5/682* (2013.01); *A61B 7/003* (2013.01); *A61N 1/0548* (2013.01); *A61N 1/36031* (2017.08); *A63B 23/032* (2013.01); *G16H 20/40* (2018.01); *A61B 5/4818* (2013.01); *A61N 1/0452* (2013.01)

(58) Field of Classification Search
CPC .............. A61N 1/3601; A61N 1/36031; A61N 1/0548; A61N 1/0452; G16H 20/40; A61B 5/0088; A61B 5/038; A61B 5/0538; A61B 5/682; A61B 7/003; A61B 5/4818; A63B 23/032
USPC .......................................................... 607/42
See application file for complete search history.

(56) References Cited

U.S. PATENT DOCUMENTS

| | | |
|---|---|---|
| 5,190,053 A | 3/1993 | Meer |
| 5,265,624 A | 11/1993 | Bowman |

(Continued)

FOREIGN PATENT DOCUMENTS

| | | |
|---|---|---|
| CN | 101590302 | 12/2009 |
| CN | 101596340 A | 12/2009 |

(Continued)

OTHER PUBLICATIONS

Joerg Steier, Chest, Original Research, Sleep Disorders; Continuous Transcutaneous Submental Electrical Stimulation in Obstructive Sleep Apnea.

*Primary Examiner* — Erin M Piateski
(74) *Attorney, Agent, or Firm* — Shay Glenn LLP

(57) ABSTRACT

A device (103) for applying an electrical stimulation to one or more muscles of the mouth of the user, the device (103) includes one or more electrodes (132, 133) for applying electrical stimulation to one or more muscles of the mouth of a user and a sensor (140*a*, 140*b*, 141*a*, 141*b*) for determining the muscle tone of the tongue of the user. Also disclosed are methods and systems for determining a stimulation plan.

18 Claims, 8 Drawing Sheets

(51) Int. Cl.
  *G16H 20/40*   (2018.01)
  *A61N 1/04*   (2006.01)

(56) References Cited

U.S. PATENT DOCUMENTS

| | | | |
|---|---|---|---|
| 5,284,161 | A | 2/1994 | Karell |
| 5,490,520 | A | 2/1996 | Schaefer et al. |
| 6,212,435 | B1 | 4/2001 | Lattner et al. |
| 7,890,193 | B2 † | 2/2011 | Tingey |
| 8,744,589 | B2 | 6/2014 | Bolea et al. |
| 9,717,904 | B2 | 8/2017 | Simon et al. |
| 9,833,613 | B2 | 12/2017 | Sama |
| 9,974,473 | B2 † | 5/2018 | Gribb |
| 10,058,701 | B2 | 8/2018 | Sama |
| 10,463,850 | B2 | 11/2019 | Fisk et al. |
| 10,561,836 | B2 | 2/2020 | Sama |
| 10,596,366 | B2 † | 3/2020 | Sama |
| 10,646,319 | B2 | 5/2020 | Johansson et al. |
| 2003/0003422 | A1 | 1/2003 | Pasquantonio et al. |
| 2005/0038485 | A1 | 2/2005 | Ludwig et al. |
| 2007/0123950 | A1 | 5/2007 | Ludlow et al. |
| 2007/0173893 | A1* | 7/2007 | Pitts .................. A61N 1/36017 607/2 |
| 2009/0048647 | A1 | 2/2009 | Tingey |
| 2009/0210032 | A1 | 8/2009 | Beiski et al. |
| 2010/0087893 | A1 | 4/2010 | Pasquet |
| 2010/0087896 | A1 | 4/2010 | McCreery |
| 2010/0204747 | A1 | 8/2010 | Lindquist et al. |
| 2011/0112601 | A1 | 5/2011 | Meadows |
| 2011/0155143 | A1 | 6/2011 | Shantha |
| 2014/0093832 | A1 | 4/2014 | Nemeh et al. |
| 2014/0135868 | A1* | 5/2014 | Bashyam ............ A61N 1/3601 607/42 |
| 2014/0277323 | A1 | 9/2014 | Tingey |
| 2014/0323839 | A1 | 10/2014 | McCreery |
| 2015/0093716 | A1 | 4/2015 | Fulton, III |
| 2015/0142120 | A1 | 5/2015 | Papay |
| 2015/0190630 | A1 | 7/2015 | Kent et al. |
| 2016/0106976 | A1* | 4/2016 | Kucklick ............ A61N 1/0548 607/42 |
| 2016/0158093 | A1* | 6/2016 | Amblard ............... A61H 23/02 601/46 |
| 2017/0143257 | A1 | 5/2017 | Kent et al. |
| 2017/0143259 | A1 | 5/2017 | Kent et al. |
| 2017/0143960 | A1* | 5/2017 | Kent .................... A61B 5/4818 |
| 2017/0224987 | A1 | 8/2017 | Kent et al. |
| 2018/0036531 | A1 | 2/2018 | Schwarz et al. |
| 2020/0121921 | A1 | 4/2020 | Sama |
| 2020/0121984 | A1 | 4/2020 | Sama |
| 2020/0164205 | A1 | 5/2020 | Sama |
| 2020/0346016 | A1 | 11/2020 | Caparso et al. |

FOREIGN PATENT DOCUMENTS

| | | |
|---|---|---|
| CN | 102548610 A | 7/2012 |
| EP | 0122102 | 10/1984 |
| EP | 1365832 | 10/2019 |
| GB | 1038829 | 8/1966 |
| JP | 2000511087 A | 8/2000 |
| JP | 2014 158607 | 9/2014 |
| JP | 2015093133 A | 5/2015 |
| RU | 2223798 | 2/2004 |
| RU | 2457006 | 7/2012 |
| TW | 615168 | 2/2018 |
| WO | 1992/015364 | 9/1992 |
| WO | 9215364 | 9/1992 |
| WO | 1997018854 | 5/1997 |
| WO | 2000029063 | 5/2000 |
| WO | 2002/0066111 | 1/2002 |
| WO | WO2005/072821 A1 | 8/2005 |
| WO | WO2006/001644 A1 | 1/2006 |
| WO | 2008/100779 | 8/2008 |
| WO | WO2009/127947 A2 | 10/2009 |
| WO | WO2013/144710 A1 | 10/2013 |
| WO | WO2020/081831 A1 | 4/2020 |
| WO | WO2022/118028 | 6/2022 |

\* cited by examiner
† cited by third party

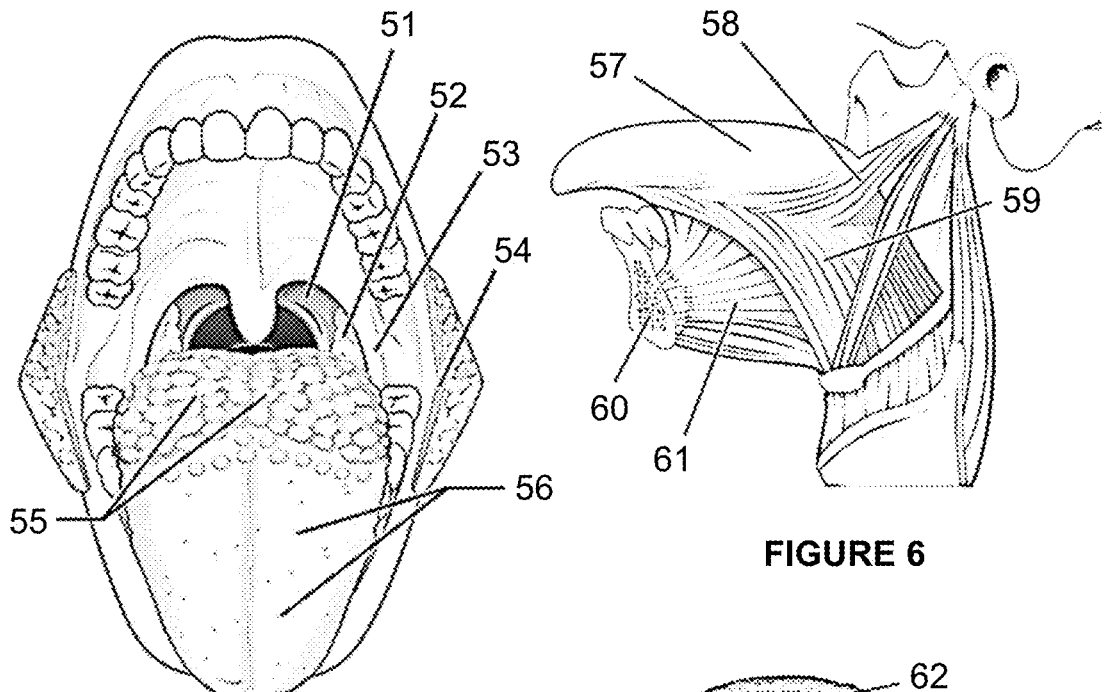
FIGURE 5
FIGURE 6
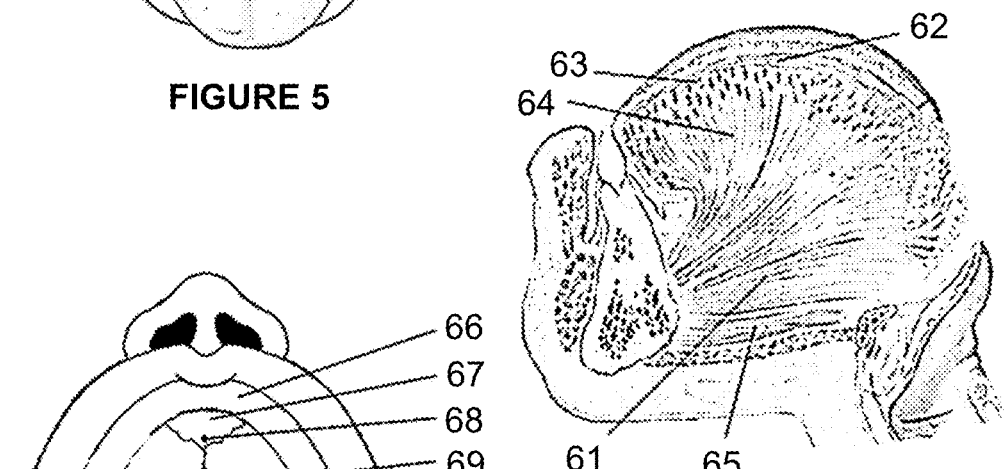
FIGURE 7
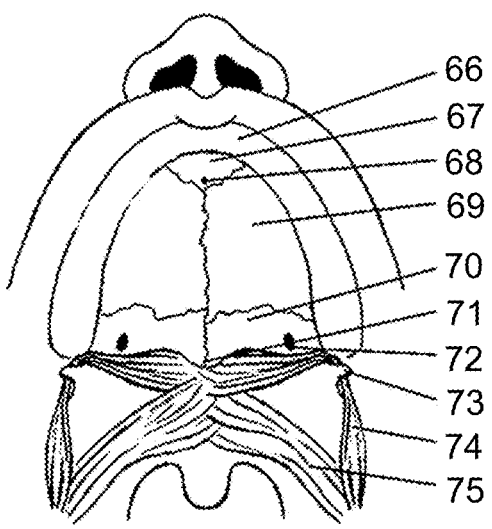
FIGURE 8
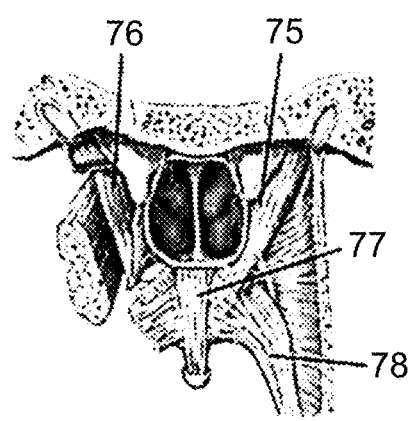
FIGURE 9

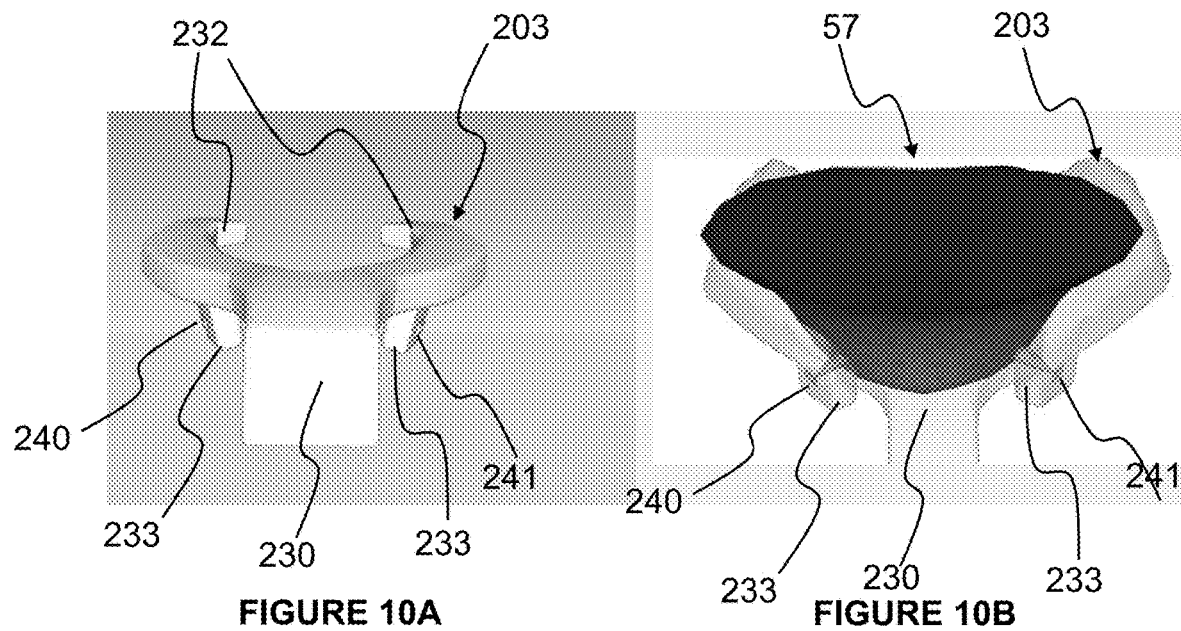
FIGURE 10A FIGURE 10B
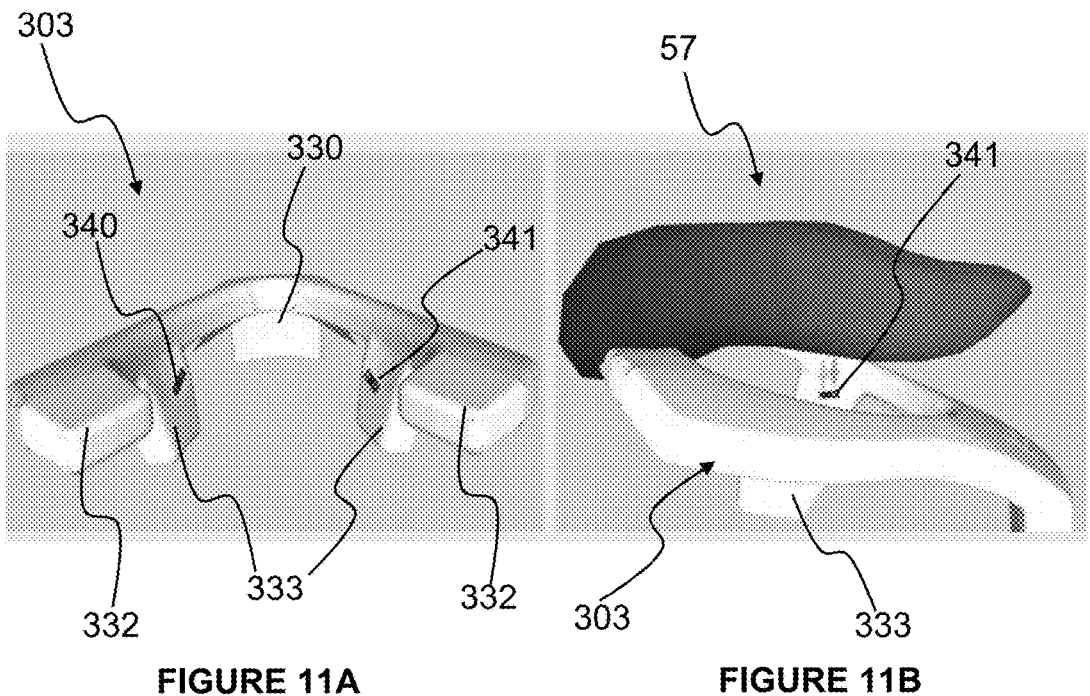
FIGURE 11A FIGURE 11B

ORAL MUSCLE TRAINING

This invention relates generally to oral muscle training, particularly to oral muscle training devices, methods, systems, and control software. More specifically, although not exclusively, this invention relates to devices and systems for determining the parameters of a stimulation plan, and/or measuring the progress of a stimulation plan, for the training of muscles of the mouth for the treatment of sleep disordered breathing.

Snoring and sleep apnoea are considered as part of a range of conditions often termed as sleep disordered breathing (SDB), with symptoms relating to disordered breathing patterns during sleep. SDBs are not only a nuisance, but they can also result in health problems, for example frequent waking from sleep, light sleeping, strain on the heart, low oxygen levels in the blood, headaches and fatigue. Further SDB can also affect the symptomatic's sleeping partner by causing disturbed sleep.

The breathing passage of humans between the throat, back of the nose and mouth, to the level of the larynx, is a collapsible tube. It has been observed that collapse of the breathing passage occurs at a positive airway pressure in individuals who snore and/or suffer from sleep apnoea syndrome and at a negative airway pressure in individuals who do not.

In an effort to address this phenomenon, treatments have been developed which include using a continuous positive airway pressure device to keep the breathing passage open or wearing a mandibular advancement device to hold the jaw and tongue forward in order to increase the space at the back of the throat.

These devices can cause discomfort such as a dry throat, they address the symptoms only temporarily, rather than addressing the underlying cause, and they must be used during sleep on an ongoing basis. As a result, users find it difficult to fall asleep or remain asleep and compliance is therefore low. Therefore, it is desirable to provide a stimulation that does not require the regular use of such devices during sleep and that addresses the underlying cause or causes of the condition.

Recent research studies have shown that implanting electrical nerve stimulators into the tongue and diaphragm are effective in the treatment of obstructive sleep apnoea. This involves intrusive surgery to implant sensors and electrodes on nerves in these areas. The device identifies an episode of obstruction using the sensors and stimulates the tongue nerve to cause contraction to relieve the obstructive event. As with pacemakers, this approach leads to maintenance and other complications, such as battery replacement, risks associated with electrical fields and issues related to external security detection devices. In addition, stimulation only occurs during an obstructive episode during sleep; it does not address the underlying cause of the condition.

In our earlier U.S. Pat. No. 9,833,613, we disclose a device for the treatment of SDB wherein a user is able to train muscles of the mouth to improve muscle tone and thereby stop, or at least inhibit, SDB events. The user will typically apply the device whilst in an awake state to improve muscle tone. In one embodiment the device has a mouthpiece for location between the upper and lower mandible arches and a pair of flanges for engaging the upper or dorsal surface of the tongue and a pair of flanges for engaging the sublingual surface of the tongue, each of the flanges including an electrode. Energising the device causes, in an embodiment, an electric current to be applied to the tongue between the sublingual and dorsal surfaces to target the genioglossus muscle and thereby improve tongue muscle tone.

Whilst the device disclosed in our previous patent is clinically proven to reduce SDB events, there is not yet disclosed a device, method or system of initially determining the parameters for therapy sessions (e.g. the current, frequency, and duration) for the development of a stimulation plan for a new patient, and/or for measuring the progress of an ongoing stimulation plan of a current patient.

A stimulation plan may comprise a number, for example a set number of stimulation sessions (e.g. plural stimulation sessions). During a stimulation session, a device may be inserted into the patient's mouth and the device energised for a period of time. Each stimulation session within the stimulation plan comprises or consists of one or more parameters that may be fixed or variable during or between stimulation sessions. Such parameters may include one or more of the stimulation time, and/or the intensity (amplitude) of the current delivered by one or more electrodes on the device, the frequency of the applied current, pulse width, pulse duration, type of current, the current application time, continuous or bursts of current. If the device comprises more than one electrode or set of electrodes, for example, a first set that engages the dorsal surface of the tongue, and a second set that engages the sublingual surface of the tongue, it may also be possible that each set of electrodes delivers, for example a different current, different intensity of electric current, different frequency of current and so on. Further, the direction of stimulation (vertical, e.g. sublingual to dorsal, lateral, e.g. sublingual to sublingual, or vertically diagonal, e.g. right dorsal to left sublingual) may be altered one or more times during a stimulation session or between successive stimulation sessions within a stimulation plan.

The treatment requirements for the use of such a device will vary from patient to patient. Consequently, it would be advantageous for a device, method, or system to exist that enables the development of one or more tailored stimulation sessions within a stimulation plan, according to the user's status at the beginning of a stimulation plan. It would also be advantageous to be able to measure the progress and/or the efficacy of a stimulation plan, such that the parameters of one or more future stimulation sessions may be tailored to the user's progress during the stimulation plan and/or responsiveness to previous stimulation sessions within the stimulation plan.

It is therefore a first non-exclusive object of the invention to provide a stimulation system, preferably to be used in an awake state, that enables the aforementioned measurements of initial patient status and/or patient progress on a stimulation plan, to be performed.

Accordingly, a first aspect of the invention provides an apparatus, e.g. an electrical stimulation device, for training oral muscle tone, the apparatus comprising a mouthpiece having at least one electrode means associated with the mouthpiece, electrical circuitry operatively connected to the electrode means, wherein the apparatus is configured to provide, in use, via the at least one electrode means electrical stimulation to one or more oral muscles, e.g. tongue muscle and optionally palate muscles, through the lining of the mouth, for example the oral mucosa, e.g. to increase resting muscle tone and/or muscle tone during sleep, the apparatus further comprising a measuring means for measuring or determining the muscle tone of the one or more oral muscles.

The measuring means may comprise one or more sensors associated with the or mounted or mountable on the apparatus, e.g. on the mouthpiece, for measuring, determining or detecting the muscle tone of the one or more oral muscles of the user, i.e. the patient. The measuring means may be passive, requiring no conscious interaction by the user, or active, where the user performs one or more specific interactions with the measuring means and/or device.

The measuring means may comprise one or more pressure sensors. The one or more pressure sensors may be used or usable to detect the pressure exerted by one or more oral muscles of the user, e.g. muscles within the tongue of the user. The one or more pressure sensors may be used or usable to detect the maximum pressure exerted by one or more oral muscles of the user, e.g. muscles within the tongue of the user. Additionally or alternatively, the one or more pressure sensors may be used or usable to detect the maximum time that the user is able to exert a target pressure with one or more oral muscles, e.g. muscles within the tongue of the user.

In embodiments in which the measuring means comprises one or more pressure sensors, the one or more pressure sensors may be provided by one or more force sensors. Different types of force sensors are known to the skilled person and include force sensing capacitors, and force sensing resistors. The measuring means, e.g. the one or more sensors, may be used or usable to measure the relative change in force, and/or the rate of change in force, and/or a force threshold value, which is applied to the measuring means, e.g. one or more sensors associated with the or mounted or mountable on the apparatus. The measuring means, e.g. the one or more sensors, may be used or usable to measure a specified and/or maximum force over a specific period of time.

The electrical circuitry of the mouthpiece may also be operatively connected to the measuring means.

It has been surprisingly found that measurements taken from the pressure exerted by the tongue muscle of the user, i.e. the patient, may be converted into measurements of muscle tone, such that the user may monitor the progress of their stimulation plan, and/or adjust their stimulation plan according to the measurements of the measuring means.

In embodiments, the measuring means may comprise one or more sensors suitable for use in recording a mechanomyogram (MMG) of one or more muscles. The measuring means may comprise one or more microphones. In embodiments, the measuring means may comprise one or more MEMS (microelectro-mechanical systems) microphones, for example, an analog silicon MEMS microphone, e.g. an AKU340® made by Akustica, Inc. of the Bosch Group (Gerlingen, Germany).

It has been found that, during contraction of one or more tongue muscles, there is a change in mechanical vibrations produced by those muscles. One or more sensors comprising one or more microphones, e.g. one or more MEMS microphones, may be configured to detect changes in the mechanical vibrations produced by the tongue muscles of the user. The data may be used to record a mechanomyogram (MMG), which is usable to determine changes in the muscle fibre. This is indicative of the muscle tone of the tongue of the user. In this way the apparatus is able to measure the muscle tone of the one or more oral muscles.

Advantageously, the use of one or more microphones, e.g. MEMS microphones, as a sensor to measure muscle tone of one or more oral muscles is a passive process. That is, the user does not need to actively interact with the mouthpiece in order for the device to determine the muscle tone of the tongue of the user. More advantageously, MEMS microphones may exhibit lower power consumption in comparison to sensors that require active interaction of the user.

In embodiments, the measuring means may be configured to make optical measurements. For example, the measuring means may comprise one or more optical reflectance sensors, e.g. one, two, or more optical reflectance sensors.

It has been found that optical reflectance sensors are usable to measure the partial pressure of oxygen in the peripheral circulation ($SpO_2$) of one or more muscles in the tongue of the user. These measurements are usable to determine the increase in vascularity of the muscles, which in turn, may be used to determine muscle function, and specifically to determine the muscle tone of the tongue of the user.

In embodiments, the measuring means may comprise one or more optical transmission sensors, e.g. one, two, or more optical transmission sensors. Such optical transmission sensors comprise an emitter and a receiver or detector.

It has been found that optical transmission sensors are usable to record the partial pressure of oxygen in the peripheral circulation ($SpO_2$) of one or more muscles in the tongue of the user. In embodiments, the one or more optical transmission sensors may be configured to operate (e.g. emit and detect) at a near IR wavelengths (800-2500 nm), for example at wavelengths of approximately 810 nm. It has been found that this wavelength may be particularly suitable to enable high cutaneous penetration, e.g. to pass through the muscle tissue. It has been found that the difference in the optical transmission through the tongue muscle is usable to determine changes in the muscle tone and vascularity of the muscle of the user.

The measuring means may comprise optical reflectance sensors, luminescence sensors and so on.

Advantageously, the measuring means, e.g. the use of optical transmission sensors, in the apparatus of the device may be integrated into a system configured to provide feedback information to the user on changes, e.g. improvements, to the muscle tone of their tongue.

Additionally or alternatively, the measuring means may include an impedance sensing system to determine or monitor the impedance across the tongue before, during and/or subsequent to a treatment session or treatment plan. The measuring means may include electrodes for use in the determination of impedance. In an embodiment the electrodes of the mouthpiece may be used to monitor or determine impedance of the tongue. In other embodiments, the impedance measurements may be effected using other or dedicated electrodes.

It has been found that treatment causes significant changes in the impedance of the tongue and thus the resistance, reactance and phase shift of stimulation (e.g. phase shift of stimulation pulses) can be determined. These measurements can be used to determine the status of the tongue muscle and may be used or be usable to 'image' the tongue muscle and thus may be able to provide a dynamic visualisation or graphical representation of progress.

This information may be used to recommend further treatment sessions, regimes, and/or plans.

Research has demonstrated that increasing the pharyngeal muscle activity or tone reduces the collapsibility of the airway and the invention disclosed in our earlier U.S. Pat. No. 9,833,613 is based on the realisation that electrical stimulation, particularly neuromuscular electrical stimulation, can be used to stimulate the muscles of the tongue and/or palate and/or the sensory nerves to improve muscle power and tone recovery.

When a person is awake, the collapsible segment of the breathing passage is kept open due to the tone of the muscles that control this area. When a person is asleep, this muscle tone reduces significantly. Evidence has shown that this reduction of muscle tone is significantly greater in individuals who suffer from obstructive sleep apnoea, less so in those who snore and notably less in individuals who suffer from neither of these disorders.

The present invention provides a measuring means that is associated with the apparatus, e.g. an electrical stimulation device, which is able to measure the muscle tone of one or more oral muscles of the user such that the user and/or another (for example a healthcare professional) is able to monitor the progress of the user's stimulation plan. By using the data generated for the muscle tone of one or more oral muscles of the user, the stimulation plan can be modified in response to measured data. For example, a processor can determine progress or change in muscle tone compared to an expected or predicted value and alter the stimulation plan accordingly. Additionally or alternatively, the change in tone might be communicated to the user (or another) for example visually, aurally or otherwise.

In an embodiment data relating to muscle tone may be provided to a computer software program (for example an APP held on a computing device) for display of tone data, for example showing changes in tone data over time.

The or a computer software program may be able to process received tone data, for example to modify a stimulation plan.

For example, if the user's muscle tone is not progressing as expected given the stimulation plan, the or a computer software program can adjust the stimulation plan, for example by increasing one or more of the characteristics of the electrical stimulation (intensity, current, duration and so on) to seek to improve muscle tone. Conversely, if the user's muscle tone is improving more than expected given the stimulation plan the or a computer software program can adjust the stimulation plan, for example by decreasing one or more of the characteristics of the electrical stimulation (intensity, current, duration and so on).

Additionally or alternatively, the user may manually select a new stimulation plan based on the change in muscle tone data.

In an embodiment, a computer software program on a computing device (e.g. an APP held on a portable computing device) is operable to recommend a future stimulation plan, and/or modifications to stimulation sessions within an existing stimulation plan, in response to the user requirements and/or the progress on a current stimulation plan. For example, the recommendations may include to increase or decrease the intensity of the electric current being supplied by one or more electrodes on the device. Additionally or alternatively, the recommendations may include to increase or decrease the set time of one or more therapy sessions within a stimulation plan.

The apparatus may further comprise a control means, e.g. a controller or a control unit, which may be programmed or programmable, for example, to activate and/or control the measuring means. The control means, e.g. a controller or a control unit, which may be programmed or programmable, for example, to activate and/or control the electrodes.

The controller or control unit may comprise one or more dials for varying the output of the apparatus, and/or for initiating or halting a test event, e.g. a muscle tone measurement event. The control unit may interface with, for example, the or a computer software program held on the or a computing device, for example the or an APP held on a mobile device, such as a personal computer, smart phone or tablet. The computer software program may be programmed to conduct a measurement of a parameter, e.g. the pressure applied by the user using one or more oral muscles to a pressure sensor, for example, for a predetermined period of time. The computer software program may be programmed to conduct a measurement of a parameter, e.g. the impedance, the sound of the muscles, the partial pressure of oxygen in the peripheral circulation or the transmission of light through the muscle mass. The control means (controller or control unit) may comprise a control system and/or a controller and/or may comprise or be at least partially comprised in the electrical circuitry.

In some embodiments, the control means may be for or configured or operable to control and/or adjust one or more parameters of measurements taken by the measuring means, for example, measurement time for measuring the muscle tone of one or more oral muscles of the user.

The device or control means may be configured or programmed to control one or more features of the muscle tone measurement. The device or control means may be operable or programmable to create and/or alter the predetermined stimulation regime, for example by a device to which the electrical stimulation device is connected, e.g. in response to the data collected by the measuring means on the muscle tone of the one or more oral muscles of the user.

The apparatus may comprise switch means operable to transform the apparatus from stimulation mode, whereby a stimulation session may be provided by the apparatus, to a test mode (and vice versa), whereby the muscle tone of the user can be assessed. The switch means may be under user control and/or under control of the controller or control means. Said switch means may be operable directly, for example by the user causing a switch to switch on the apparatus, or remotely, for example by accessing a computing device linked to the apparatus (e.g. via an APP on a personal computing device such as a PC, smartphone, tablet and so on).

In embodiments, the mouthpiece may comprise one or more arms and/or one or more appendages or flanges which may extend from the one or more arms, e.g. for contacting one or more oral muscles. At least one arm and/or at least one appendage or flange may be flat or planar, for example with major surfaces. Optionally, the mouthpiece may comprise a pair of arms each of which may comprise one or more appendages or flanges. In some embodiments, the mouthpiece comprise a pair of arms that may extend at least partially alongside each other and/or at an angle relative to one another and/or parallel to each other. For example, the mouthpiece may comprise a pair of arms joined together at one end and diverging from one another, for example in a substantially V-shape or U-shape or horseshoe shape.

The one or more appendages or flanges may extend inwardly of the pair of arms, e.g. from one arm and toward the other arm. In some embodiments, each arm comprises at least one appendage or flange, for example opposite one another and/or extending toward one another. In embodiments, each arm comprises two or more appendages or flanges, for example an appendage or flange extending from a free end of each arm and/or an appendage or flange extending from an intermediate portion of each arm.

At least one appendage or flange may be curved, e.g. a flat curved shape or member, and/or extend upwardly or downwardly or out of the plane of the mouthpiece or at least one arm thereof. At least one appendage or flange may be shaped to cooperate or approximate or accommodate a tongue surface, for example a dorsal tongue surface or a sublingual tongue surface. In embodiments, the mouthpiece comprises at least one appendage or flange that is shaped to cooperate or approximate or accommodate a dorsal tongue surface and at least one appendage or flange that is shaped to cooperate or approximate or accommodate a sublingual tongue surface. In embodiments having a pair of arms, each arm may comprise an appendage or flange shaped to cooperate or approximate or accommodate a dorsal tongue surface and an appendage or flange that is shaped to cooperate or approximate or accommodate a sublingual tongue surface.

At least one of the appendages or flanges may comprise one or more electrodes or series thereof. At least one electrode or series of electrodes may be adjacent and/or associated with and/or exposed at a surface, e.g. a major surface, of the at least one appendage or flange. In embodiments, at least one of the appendages or flanges comprises electrodes associated with each of its major surfaces. The electrodes associated with one of the major surfaces may be isolated and/or controllable independently from another or the other major surface thereof. Additionally or alternatively, the electrodes of or associated with one appendage or flange may be isolated and/or controllable independently from at least one other appendage or flange.

In embodiments, the mouthpiece may comprise a pair of arms joined together at one end and diverging from one another to provide a substantially horseshoe shape with one or more flanges extending inwardly from at least one arm, the or each flange comprising electrode means. The mouthpiece may comprise a pair of flanges each extending inwardly from a respective arm, which flanges are shaped to accommodate a dorsal tongue surface. The mouthpiece may comprise a pair of flanges each extending inwardly from a respective arm, which flanges are shaped to accommodate a sublingual tongue surface. Each of the pair of flanges may be shaped to accommodate a dorsal tongue surface extends from at or adjacent a free end of the arm and/or each of the pair of flanges may be shaped to accommodate a sublingual tongue surface extends from an intermediate portion of the arm.

In embodiments, the measuring means, e.g. one or more sensors and/or one or more pressure sensors, microphones (e.g. MEMS microphones), optical reflectance sensors, impedance sensors and/or optical transmission sensors; may be located or locatable on the mouthpiece. In embodiments, the measuring means, e.g. one or more sensors and/or one or more pressure sensors, microphones (e.g. MEMS microphones), optical reflectance sensors, and/or optical transmission sensors; may be located or locatable, where present, on one or more flange(s). For example, a first sensor, e.g. a pressure sensor, a microphone (e.g. a MEMS microphone), an optical reflectance sensor, impedance sensor and/or an optical transmission sensor; may be located or locatable on a first flange that is shaped to accommodate the dorsal surface of the tongue, and/or a second sensor, e.g. a pressure sensor, a microphone (e.g. a MEMS microphone), an optical reflectance sensor, impedance sensor and/or an optical transmission sensor; may be located or locatable on a second flange that is shaped to accommodate the dorsal surface of the tongue. Additionally or alternatively, a first sensor, e.g. a pressure sensor, a microphone (e.g. a MEMS microphone), an optical reflectance sensor, impedance sensor and/or an optical transmission sensor; may be located or locatable on a first flange that is shaped to accommodate the sublingual surface of the tongue, and/or a second sensor, e.g. a pressure sensor, a microphone (e.g. a MEMS microphone), an optical reflectance sensor, impedance sensor and/or an optical transmission sensor; may be located or locatable on a second flange that is shaped to accommodate the sublingual surface of the tongue. In embodiments, one or more sensor(s) is located proximal or adjacent to the one or more electrodes.

Additionally or alternatively, one or more sensors may be located or locatable on one of, or both of, the pair of arms of the mouthpiece.

Another aspect of the invention provides an electrical stimulation device for training one or more oral muscles, for example a trans mucosal neuromuscular electrical stimulation device, the device comprising a mouthpiece, electrode means associated with the mouthpiece and electrical circuitry operatively connected to the electrode means, wherein the mouthpiece comprises a pair of arms joined together at one end and diverging from one another with one or more flanges extending inwardly from at least one arm, the or each flange including at least part of the electrode means associated therewith for providing electrical stimulation to one or more oral muscles, the electrical stimulation device further comprising a measuring means for measuring the muscle tone of the one or more oral muscles.

Yet another aspect of the invention provides an electrical stimulation mouthpiece for training one or more oral muscles, for example a trans mucosal neuromuscular electrical stimulation mouthpiece, the mouthpiece comprising a pair of arms joined together at one end and diverging from one another with one or more flanges extending inwardly from at least one arm, wherein the or each flange includes electrode means associated therewith for providing electrical stimulation to one or more oral muscles, the electrical stimulation device further comprising a measuring means for measuring the muscle tone of the one or more oral muscles.

For the avoidance of doubt, any of the features described herein apply equally to any aspect of the invention.

The apparatus is preferably configured to provide a current, for example an electric current or impulse current, which may be selected from one or more of a Russian current, interferential current, pre-modulated current, DC electric current, biphasic electric current or impulse current. Other current forms may be used.

By providing a biphasic electric current, particularly a biphasic electric impulse current, tongue and/or palate muscles contributing to the collapsibility of the airway can be stimulated along with the sensory nerves to increase resting muscle tone and muscle tone during sleep.

The current is preferably a biphasic symmetrical current, but it may additionally or alternatively be a biphasic asymmetrical current that may either be balanced or unbalanced. The device or electrical circuitry may be configured to provide, in use, via the electrode means an electric current with a frequency of up to 150 Hz, say between 1, 2, 3, 4 or 5 Hz and 150 Hz.

The electric current may comprise a frequency of between 10 and 140 Hz, for example between 15 and 130 Hz, preferably between 20 and 120 Hz. Preferably, the electric current comprises a frequency of between 1 and 50 Hz and/or between 2 and 120 Hz.

The device or electrical circuitry may be configured to provide two or more currents, for example a first current and/or a second current, which second current may be different from and/or configurable or settable independently from the first current. At least one, e.g. both, of the first and/or second current may comprise a biphasic (or other) current, each of which is preferably symmetrical, but may be asymmetrical and either balanced or unbalanced. At least one of the first and/or second current may comprise a frequency of between 1, 2, 3, 4, 5 and 150 Hz, for example between 1 and 140 Hz, e.g. between 1 and 130 Hz, preferably between 2 and 120 Hz. In some embodiments, one or the currents may comprise a frequency of between 2 and 50 Hz and/or the other current may comprise a frequency of between 1 and 120 Hz.

The inventors believe that the application of an electric current in one or each of these two frequency ranges is particularly suited to targeting tongue muscles contributing to the collapsibility of the airway.

The device or electrical circuitry may be configured to provide, in use, the or at least one or each electrical current to one or more oral muscles, such as palate and/or tongue muscles, for example through the lining of the mouth, e.g. the oral mucosa, such as to increase resting muscle tone and/or muscle tone during sleep. In some embodiments, the device is configured to provide, in use, the electrical current, e.g. the first electrical current, to one or more palate muscles. Additionally or alternatively, the device may be configured to provide, in use, the electrical current, e.g. the second electrical current, to one or more tongue muscles, e.g. via the dorsal tongue surface. Additionally or alternatively, the device may be configured to provide, in use, the electrical current, e.g. the first or second electrical current, to one or more tongue muscles via the underside of the tongue.

The mouthpiece may comprise a gripping base, which may comprise an enlarged end, e.g. an enlarged free end, which may be connected or secured to, e.g. formed integrally with, the mouthpiece or a body or one or more or each arm thereof, for example by a necked portion.

The electrode means preferably comprises at least one anode and at least one cathode, for example two or more anodes and/or two or more cathodes, e.g. a plurality of anodes and a plurality of cathodes. At least part of the electrode means, for example one or more or each or all of the electrodes, may be mounted to or on or within and/or at least partially housed or contained within the mouthpiece. In some embodiments, the mouthpiece comprises a shield or shield means, for example on one side of the electrode means, e.g. for inhibiting or preventing the electrical stimulation or current from being applied or provided by or at or from one side of the mouthpiece. Suitable materials for the shield or shield means will be apparent to those skilled in the art.

In embodiments, the electrode means is configured or operable to provide or apply, e.g. selectively, the electrical stimulation or current at or from at least one or each or both sides, for example by including the or a shielding means or shield between a first set or series of electrode means or electrodes and a second set or series of electrode means or electrodes. In some embodiments, the first electrical current is provided or applied at or from a first side, e.g. major side, of the mouthpiece and/or by the first set or series of electrode means or electrodes. Additionally or alternatively, the second electrical current may be provided or applied at or from a second side, e.g. major side, of the mouthpiece and/or by the second set or series of electrode means or electrodes. In other embodiments, the first and second electrical currents may be provided or applied from at least one or each or both sides.

The mouthpiece may be insertable into the mouth and held in place, e.g. manually. The mouthpiece may be at least partially flattened and/or substantially flat and/or paddle-shaped, for example with at least one flat and/or major surface, preferably two flat major surfaces. In some embodiments, the device may include a handle to which the mouthpiece may be connected or mounted or attached, for example rigidly and/or releasably, e.g. to enable the mouthpiece to be inserted and/or held, in use, within one or more locations or positions and/or orientations within the mouth. In some embodiments, the mouthpiece is free of any mounting means for mounting or securing it to or in or within the mouth of a user.

In embodiments, the mouthpiece may include a mounting means. The mounting means may be for mounting the mouthpiece to an upper part or portion of the mouth, for example such that the mouthpiece or the or a first side or surface thereof is or may be in contact with and/or adjacent one or more palate muscles and/or the roof of the mouth and/or the mouthpiece or the or a second side or surface thereof is or may be in contact with and/or adjacent one or more tongue muscles, for example a dorsal tongue surface. Additionally or alternatively, the mounting means may be for mounting the mouthpiece to a lower part or portion of the mouth, for example such that the mouthpiece or the or a first side or surface thereof is or may be in contact with and/or adjacent one or more tongue muscles, for example a sub-lingual tongue surface. In embodiments, the device comprises a first mouthpiece with mounting means for mounting it to an upper part or portion of the mouth and a second mouthpiece for mounting it to a lower part or portion of the mouth.

The device or handle may comprise an input means or activator, which may include one or more input devices, buttons and/or push buttons and/or switches and/or dials or the like, e.g. for enabling or activating or initiating the electrical stimulation or current, or for enabling or activating or initiating measurement of the muscle tone of the user. The device or handle may comprise a power source and/or a cable connectable to a power source. In some embodiments, the device comprises a main body that includes or incorporates or provides the handle and/or which includes or houses the power source, which may comprise a rechargeable power source or one or more batteries that may be rechargeable, and/or which can either include the cable or be operatively, e.g. inductively, connectable to a charging station that includes or incorporates the cable, for example to enable the power source to be recharged. The device may include the charging station.

In some embodiments, the device comprises an adjustment means or adjuster, e.g. a frequency adjustment means or adjuster, for adjusting the frequency of the current or of the first and/or second currents, for example a respective first and second current frequency adjustment means or adjuster for adjusting the frequency of the current, e.g. between one of the aforementioned ranges. In embodiments, the adjustment means or adjuster is a step-wise adjustment means or adjuster and/or is configured to enable a user to select from one of two or more, e.g. three, four or five, predetermined frequency settings. The device may be operable or configured to provide the first and second currents simultaneously and/or concurrently and/or in parallel. Additionally or alternatively, the device may be operable or configured to provide the first and second currents in series and/or in sequence and/or in succession.

Advantageously, the adjustment means may be used to adjust the parameters of the therapy session in response to measurements taken by the measuring mean on the muscle tone of the user.

The current or at least one, e.g. both, of the first and/or second current may comprise an impulse current. The pulse duration of the or each impulse current may be between 50 and 1000 µs, for example between 100 and 900 µs, e.g. between 150 and 800 µs, preferably between 200 and 700 µs. Preferably, the or a further adjustment means or adjuster, e.g.

an pulse duration adjustment means or adjuster, of the device is provided for adjusting the pulse duration, for example between one of the aforementioned ranges.

The electrical stimulation or current or first and/or second currents may comprise an intensity or current amplitude, which is preferably selected or selectable to provide maximum contraction of the muscles being treated. By way of example, the intensity or amplitude may comprise approximately 10 mA, for example between 1 and 100 mA, such as between 5 and 50 mA, for example between 5 and 15 mA or between 7 and 25 mA, e.g. between 8 and 12 mA. The or a further adjustment means or adjuster, e.g. an intensity or amplitude adjustment means or adjuster, may be provided for adjusting the intensity or amplitude, for example from 0 to 500 mA or from 0 to 250 mA or from 0 to 200 mA or from 0 to 150 mA or from 0 to 100 mA.

In some embodiments, the device is configured or programmed to provide the electrical stimulation or electric current or the first and/or second electric current for a predetermined period, which may comprise between 1 minute and 1 hour, for example between 5 and 30 minutes, preferably between 10 and 20 minutes. The or a further adjustment means or adjuster, e.g. a stimulation duration adjustment means or adjuster, may be provided for adjusting the stimulation duration, for example from 0 to 10 hours or from 0 to 5 hours or from 0 to 1 hour or from 0 to 30 minutes.

A further aspect of the invention provides a system for measuring the muscle tone of one or more oral muscles of a user, the system comprising:
  a) A mouthpiece held between the teeth of a user;
  b) a measuring means for measuring the muscle tone of the one or more oral muscles in or on or associated with mouthpiece
  c) optional memory means for holding data received from the measuring means
  d) processing means to process data received from the measuring means.

The mouthpiece preferably comprises electrode means for stimulating one or more muscles of the mouth.

The processing means may be operable to control and/or adjust the output of the electrode means based on the data received from the measuring means.

A yet further aspect of the invention provides a system for measuring the muscle tone of one or more oral muscles of a user, the system comprising:
  a) a mouthpiece, e.g. an electrical stimulation device, for training oral muscle tone, the device comprising a mouthpiece having at least one electrode means associated with the mouthpiece, electrical circuitry operatively connected to the electrode means, wherein the device is configured to provide, in use, via the at least one electrode means electrical stimulation to one or more oral muscles, e.g. tongue muscle and optionally palate muscles, through the lining of the mouth, for example the oral mucosa, e.g. to increase resting muscle tone and/or muscle tone during sleep;
  b) a memory means on which is stored a database for the conversion of data from the measuring means into muscle tone data;
  c) a processing means, e.g. a processor, operatively connected to the measuring means of the device and to the memory means;
wherein the system is configured, on or after a muscle tone measurement event, to determine the muscle tone of one or more oral muscles of the user, by comparing the data from the measuring means with the data within the database of the memory means, using the processing means.

In embodiments, the measuring means, for measuring the muscle tone of the one or more oral muscles in or on or associated with a device, comprises one or more pressure sensors, e.g. for measuring the pressure exerted by one or more oral muscles of the user.

The memory means may comprise a database suitable for the conversion of data, e.g. pressure data, from the measuring means, e.g. the one or more pressure sensors, into data, e.g. user readable data, on the muscle tone of the one or more oral muscles of the user. The processing means may be configured to convert data, e.g. pressure data from one or more pressure sensors, into data, e.g. user readable data, on the muscle tone of the one or more oral muscles of the user.

In embodiments, the measuring means, for measuring the muscle tone of the one or more oral muscles in or on or associated with a device, comprises one or more microphones, e.g. MEMS microphones), e.g. for measuring a mechanomyogram (MMG) of one or more oral muscles of the user. In embodiments, the memory means may comprise a database suitable for the conversion of data, e.g. mechanomyogram (MMG) data, from the measuring means, e.g. the one or more MEMS microphones, into data, e.g. user readable data, on the muscle tone of the one or more oral muscles of the user. The processing means may be configured to convert data, e.g. mechanomyogram (MMG) data from one or more MEMS microphones, into data, e.g. user readable data, on the muscle tone of the one or more oral muscles of the user.

In embodiments, the measuring means, for measuring the muscle tone of the one or more oral muscles in or on or associated with a device, comprises one or more optical reflectance sensors and/or one or more optical transmission sensors, e.g. for measuring the partial pressure of oxygen in the peripheral circulation ($SpO_2$) to determine the vascularity of one or more muscles. In embodiments, the memory means may comprise a database suitable for the conversion of data, e.g. peripheral circulation ($SpO_2$) data, from the measuring means, e.g. the one or more optical reflectance sensors and/or one or more optical transmission sensors, into data, e.g. user readable data, on the muscle tone of the one or more oral muscles of the user. The processing means may be configured to convert data, e.g. peripheral circulation ($SpO_2$) data from one or more optical reflectance sensors and/or one or more optical transmission sensors, into data, e.g. user readable data, on the muscle tone of the one or more oral muscles of the user.

In embodiments the measuring means may be operable to monitor the progressive characteristic changes in muscle structure. Such changes in structure may be captured by methods such as electrical impedance tomography using the electrodes used in stimulation and/or a dedicated one or more electrodes.

Advantageously, the system of the invention enables the user to be able to measure the muscle tone of one or more oral muscles, e.g. muscles within the tongue of the user, via a measuring means, e.g. one or more pressure sensors, or one or more microphones (e.g. MEMS microphones), or one or more optical reflectance sensors, and/or one or more optical transmission sensors, one or more impedance sensors and/or one or more luminescence or other sensors.

The or a database of the or a memory means (or at least accessible by said memory means) may further comprise values for 'normal' or 'healthy' muscle tone data, e.g. according to the rest of the population and/or a model heathy patient who does not suffer from sleep apnoea. The system may enable the user and/or a healthcare professional to compare the muscle tone data or measurement of the user with 'normal' or 'healthy' muscle tone data stored within the database. The system may enable the user and/or healthcare professional to design a future stimulation plan based on the comparison of data between the user and the values for 'normal' or 'healthy' muscle tone data.

The database of the memory means may be capable of storing data, e.g. data from previous muscle tone measurement events performed by the user. The database of the memory means may further comprise stored data from previous muscle tone measurement events performed by the user. The system may enable the user and/or healthcare professional to perform comparisons between the muscle tone data of the user over time. For example, the system may enable the user and/or healthcare professional to compare the muscle tone data or measurement of the user from a second muscle tone measurement event, with the muscle tone data or measurement of the user from a first muscle tone measurement event. The system may enable the user and/or healthcare professional to modify or tailor the therapy session within a stimulation plan based on their progress, which is established through comparison of the user's muscle tone data at specific muscle tone measurement events over time.

The database of (or accessible by) said memory means may further comprise data for the projected or targeted progress of the user on a stimulation plan based on the parameters, e.g. therapy session time, electric current intensity, electric current intensity of one or more specific electrodes, and so on, of the therapy sessions within the stimulation plan. The system may be configured to retrieve data from the database and compare the user's data from two or more previous muscle tone measurement events performed by the user with the projected or targeted progress expected on that stimulation plan, such that the system is able to make recommendations on the parameters of future therapy sessions.

Advantageously, the system is able to track the progress of the patient's stimulation plan such that the healthcare professional is able to modify or tailor the therapy sessions within the treatment plan. More advantageously, the system may be able to compare projected or targeted progress with actual progress, such that the system is able to make recommendations on the parameters for future therapy sessions within a treatment plan.

The system may further comprise an alert means, e.g. to alert the user that the device has been incorrectly located within their mouth, and/or that the system is unable to perform a measurement using the measuring means. The alert means may comprise an audible or visual alert means or device. The alert means may comprise an audible means, e.g. for providing an audible alert or indication or statement or description, e.g. that the device has been incorrectly located within the mouth of the user, and/or a display means or display, e.g. for providing a visual representation, e.g. that the device has been incorrectly located within the mouth of the user.

The system may further comprise a data transfer means or element or module or component or device, for example a port, e.g. a USB or serial port, or a wireless transmitter, e.g. a radio or Bluetooth or Wifi transmitter, for transferring data from at least one of the memory means for review or analysis. Additionally or alternatively, the system may comprise a display for displaying data stored in or on at least one of the memory means.

The system may further comprise a communication means, e.g. for communicating with a remote server, e.g. a doctor's surgery, and/or for transmitting or transferring data, for example, the muscle tone data of one or more oral muscles of the user. The communication means may comprise a communication element or module or component or device and/or may include a wireless communication or telecommunication means or system or a transmitter or wireless transmitter or receiver or a wireless receiver. Preferably, the communication means is operatively connected to the processing means. More preferably, the system is configured or programmed to cause the communication means to transmit, e.g. on or after detection of a muscle tone data, at least some of the data set, for example to a server or remote server.

The system may further comprise a server, e.g. a remote server, which may comprise a server communication means, e.g. for receiving data from the device and/or for sending data to the device. The server communication means may comprise a communication element or module or component or device and/or may include a wireless communication or telecommunication means or system or a transmitter or wireless transmitter or receiver or a wireless receiver.

Another aspect of the invention provides a computer program element comprising computer readable program code means for causing a processor to execute a procedure to implement a method, e.g. a method of measuring muscle tone, or treatment regime comprising providing electrical stimulation to one or more oral muscles, e.g. palate and/or tongue muscles, through the lining of the mouth, for example the oral mucosa, e.g. to increase resting muscle tone and/or muscle tone during sleep.

Another aspect of the invention provides a method of dynamically altering a stimulation plan, the method comprising:
 a) defining a stimulation plan for electrically stimulating one or more muscles of a mouth of a user;
 b) using a mouthpiece to electrically stimulate said one or more muscles of the mouth of a user;
 c) using the mouthpiece to measure or estimate the muscle tone of the tongue of the user;
 d) adjusting the stimulation plan according to the measured or estimated tone of the tongue of the user.

The stimulation plan preferably comprises at least two stimulation sessions to be performed by the mouthpiece on the user, for example whilst the user is in an awake state.

Step d) preferably comprises altering a successive stimulation session based on the measured tone of the tongue of the user.

A typical stimulation session may comprise stimulating the mouthpiece whilst in the mouth of the user for a certain period of time, for example less than 20 minutes. A stimulation plan may provide one or two or more stimulation sessions a day for plural days, say one, two or three months (e.g. the stimulation plan may comprise 31 or 62, 62 or 124 or 93 or 186 stimulation sessions or more). The apparatus may change successive stimulation sessions and/or the method may entail altering successive stimulation sessions depending on the tongue tone data.

A yet further aspect provides a device for applying an electrical stimulation to one or more muscles of the mouth of the user, the device comprising one or more electrodes for applying electrical stimulation to one or more muscles of the mouth of a user and a sensor to sense, determine or measure the muscle tone of the tongue of the user.

A still further aspect of the invention provides apparatus for applying an electrical stimulation to the mouth of a user, the apparatus comprising a device as stated above and a controller, the controller being operable to alter the electrical stimulation to said one or more tongue muscles based on sensed, determined or measured muscle tone of the tongue of the user sensed, determined or measured by the sensor.

The apparatus may comprise a memory means to hold data relating to one or both of the electrical stimulation which has been applied to said one or more muscles and/or data relating to the measured or sensed muscle tone of the tongue of the user. The apparatus may comprise a processor to process data relating to one or both of the electrical stimulation which has been applied to said one or more muscles and/or data relating to the measured, determined or sensed muscle tone of the tongue of the user. The processor may be operable to control the controller based on data processed by the processor.

Another aspect of the invention provides a method for measuring the muscle tone of one or more oral muscles, the method comprising:
 a) providing an apparatus, e.g. an electrical stimulation device, for training oral muscle tone, the apparatus comprising a mouthpiece having at least one electrode means associated with the mouthpiece, electrical circuitry operatively connected to the electrode means, wherein the apparatus is configured to provide, in use, via the at least one electrode means electrical stimulation to one or more oral muscles, e.g. tongue muscle and optionally palate muscles, through the lining of the mouth, for example the oral mucosa, e.g. to increase resting muscle tone and/or muscle tone during sleep, the apparatus further comprising a measuring means for measuring the muscle tone of the one or more oral muscles;
 b) locating the mouthpiece in a patient's mouth;
 c) activating the measuring means with the one or more oral muscles, e.g. tongue muscles, to collect data;
 d) converting the data into user readable muscle tone data for the one or more oral muscles of the user.

The measuring means may comprise one or more active and/or passive sensors. For example, the measuring means may comprise one or more pressure sensors, one or more audible sensors, one or more optical transmission and/or reflectance sensors, one or more impedance sensors and/or one or more luminescence sensors. Activating the one or more pressure sensors, may comprise the user applying pressure to the measuring means via one or more oral muscles, e.g. tongue muscles. This is an example of an active sensor which may require a specific interaction by the user. Passive sensors may measure, sense or determine muscle tone without any specific interaction being required by the user.

A further aspect of the invention provides a method of providing a stimulation plan, the method comprising locating a mouthpiece having one or more electrodes in the mouth of a user; using a sensor on the mouthpiece to determine the muscle tone of the tongue of the mouth of the user; generating a stimulation plan based on determined muscle tone.

A yet further aspect of the invention provides a method of altering a stimulation plan, the method comprising; providing a stimulation plan for electrically stimulating one or more muscles of a mouth of a user; locating a mouthpiece in the mouth of a user; using a sensor on the mouthpiece to determine the muscle tone of a muscle of the mouth of the user; and adjusting the stimulation plan according to the determined muscle tone of the user.

The method may further comprise providing user-related data, for example, one or more of age, weight, height, BMI. The method may also comprise comparing the determined muscle tone to a desired or expected muscle tone and adjusting the stimulation plan accordingly.

The stimulation plan preferably comprises one or more stimulation sessions. The electrodes may be controlled according to certain control paradigms during a stimulation session. The control paradigms may relate to current, current type, electrical intensity, frequency, pulse length, pulse duration, stimulation time and so on.

For example, a stimulation session may comprise a stimulation period of 20 minutes, during which a biphasic current is used to stimulate muscles, the biphasic current having a certain frequency, amplitude, pulse duration. A further or subsequent stimulation session may have the same or different characteristics.

Another aspect of the invention provides a system for applying electrical stimulation to one or more muscles of the mouth to train the muscles of the mouth for combating sleep disordered breathing, the system comprising a mouthpiece for locating in the mouth of a user, the mouthpiece having one or more electrodes and one or more sensors; a controller for controlling the one or more electrodes and the one or more sensors; a processor for providing signals to and receiving signals from the controller; and wherein the processor is operable to cause the controller to control the electrodes dependent upon signals received from the sensors.

The sensors may be pressure sensors or electrical sensors. In an embodiment the sensors may be able to determine a perturbation or attenuation of an electrical stimulation signal transmitted by the electrodes. The or a stimulation signal may propagate vertically (e.g. between a dorsal and sublingual surface of the tongue) or laterally (e.g. across a dorsal surface of the tongue), or both. The sensors may be any of those set out above.

A further aspect of the invention provides a computer program element comprising computer readable program code means for causing a processor to execute a procedure to implement the aforementioned method. A yet further aspect of the invention provides the computer program element embodied on a computer readable medium.

A yet further aspect of the invention provides a control means or control system or controller comprising the aforementioned computer program element or computer readable medium for measuring the muscle tone of one or more oral muscles, for example for controlling the method described above.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. For the avoidance of doubt, the terms "may", "and/or", "e.g.", "for example" and any similar term as used herein should be interpreted as non-limiting such that any feature so-described need not be present. Indeed, any combination of optional features is expressly envisaged without departing from the scope of the invention, whether or not these are expressly claimed. The applicant reserves the right to change any originally filed claim or file any new claim accordingly, including the right to amend any originally filed claim to depend from and/or incorporate any feature of any other claim although not originally claimed in that manner.

Embodiments of the invention will now be described by way of example only with reference to the accompanying drawings in which.

Figure 3A:
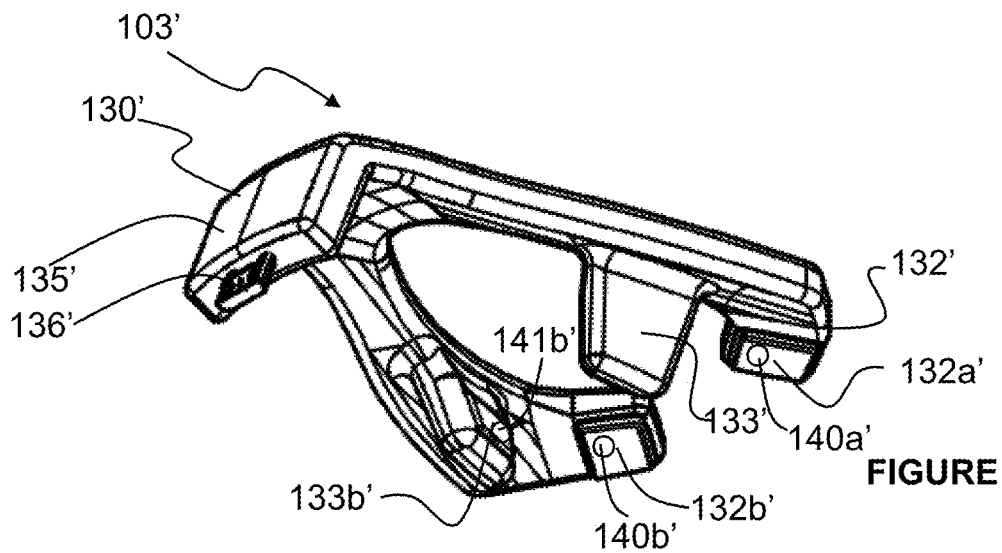
Figure 3B:
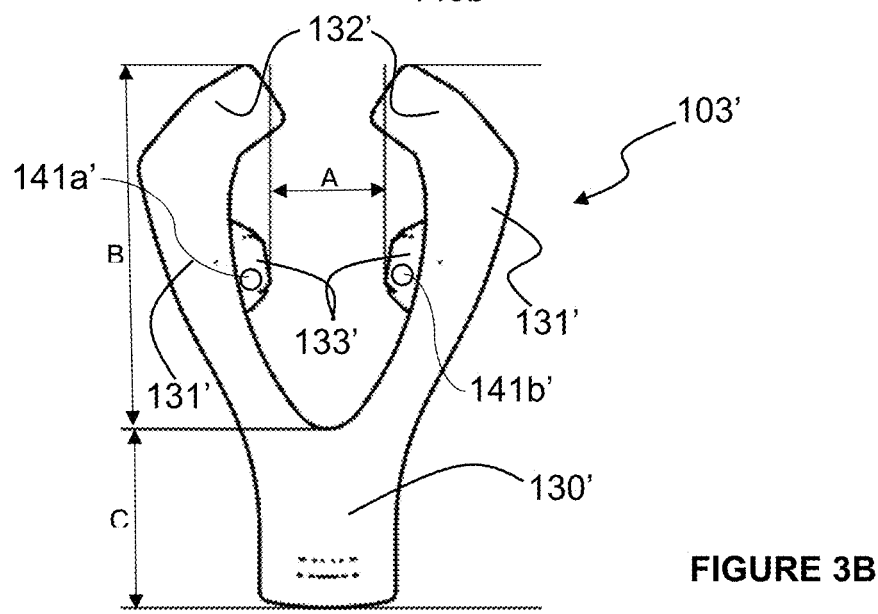
Figure 3C:
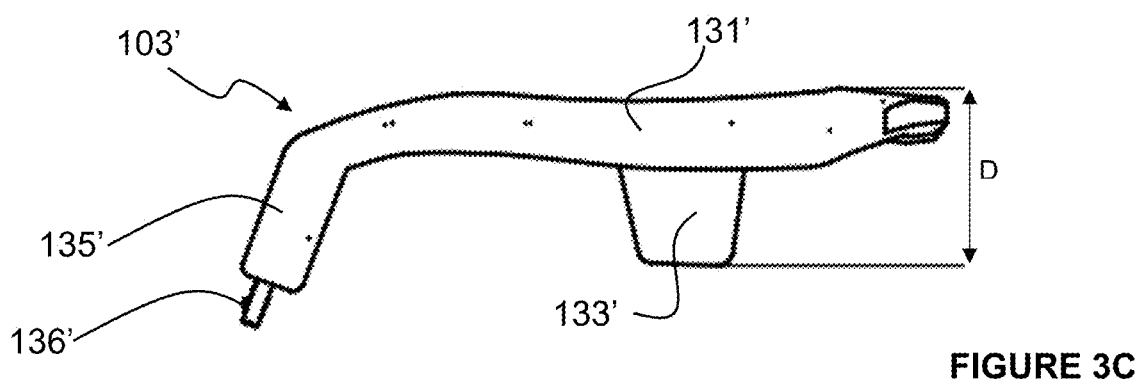
Figure 3D:
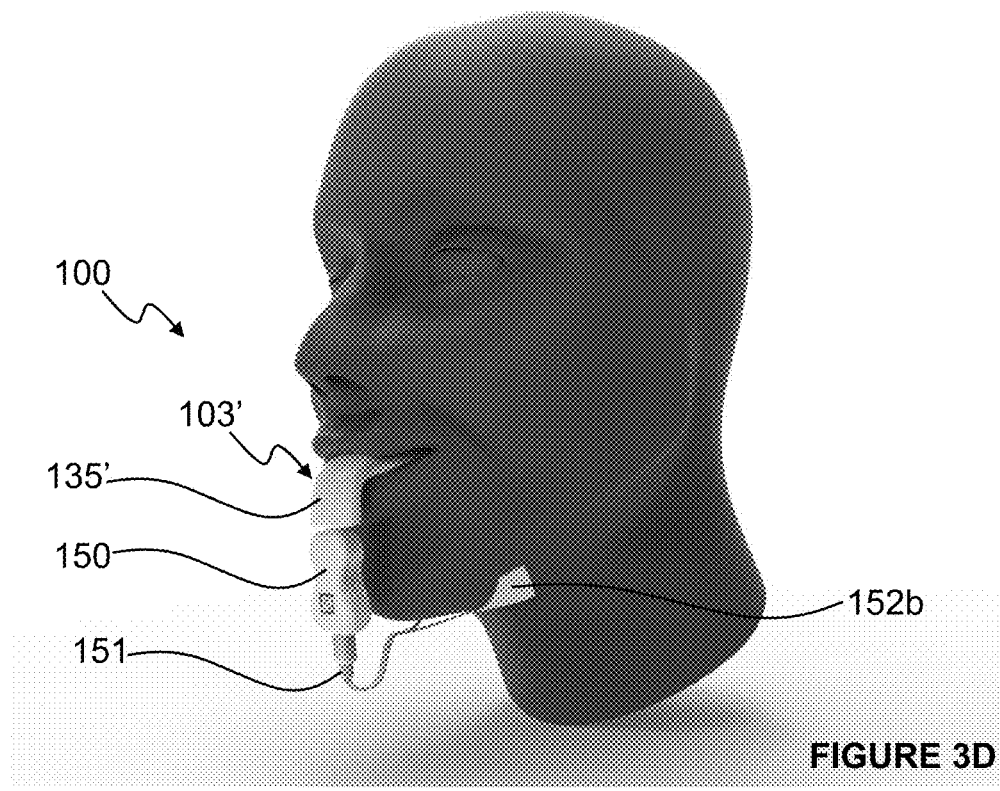
Figure 3E:
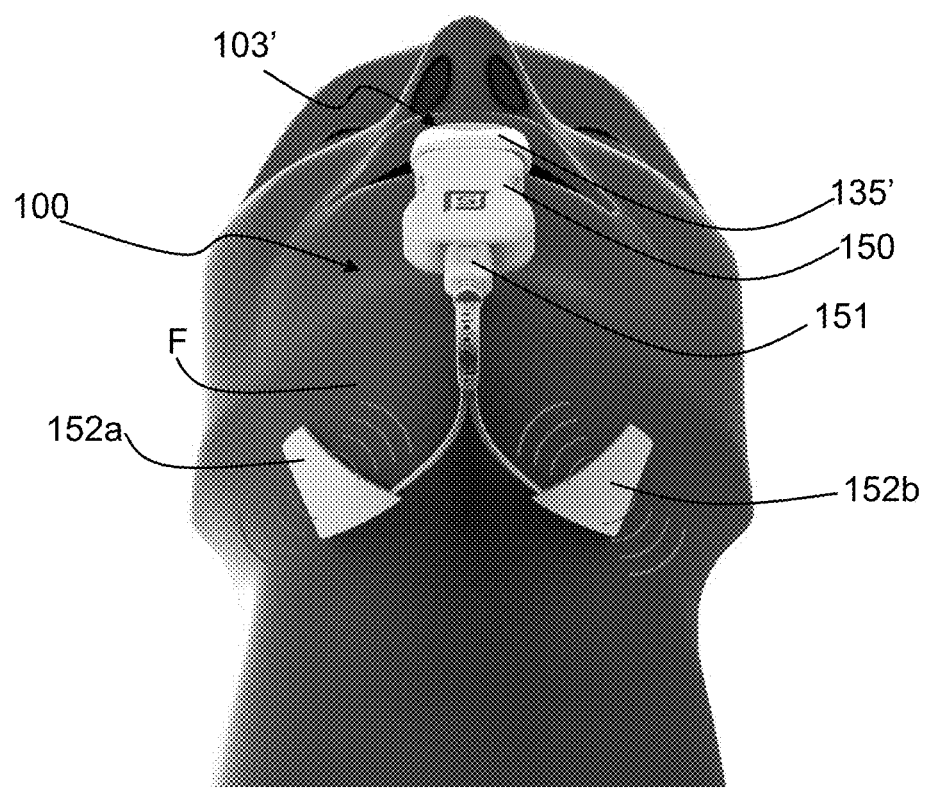
Figure 4A:
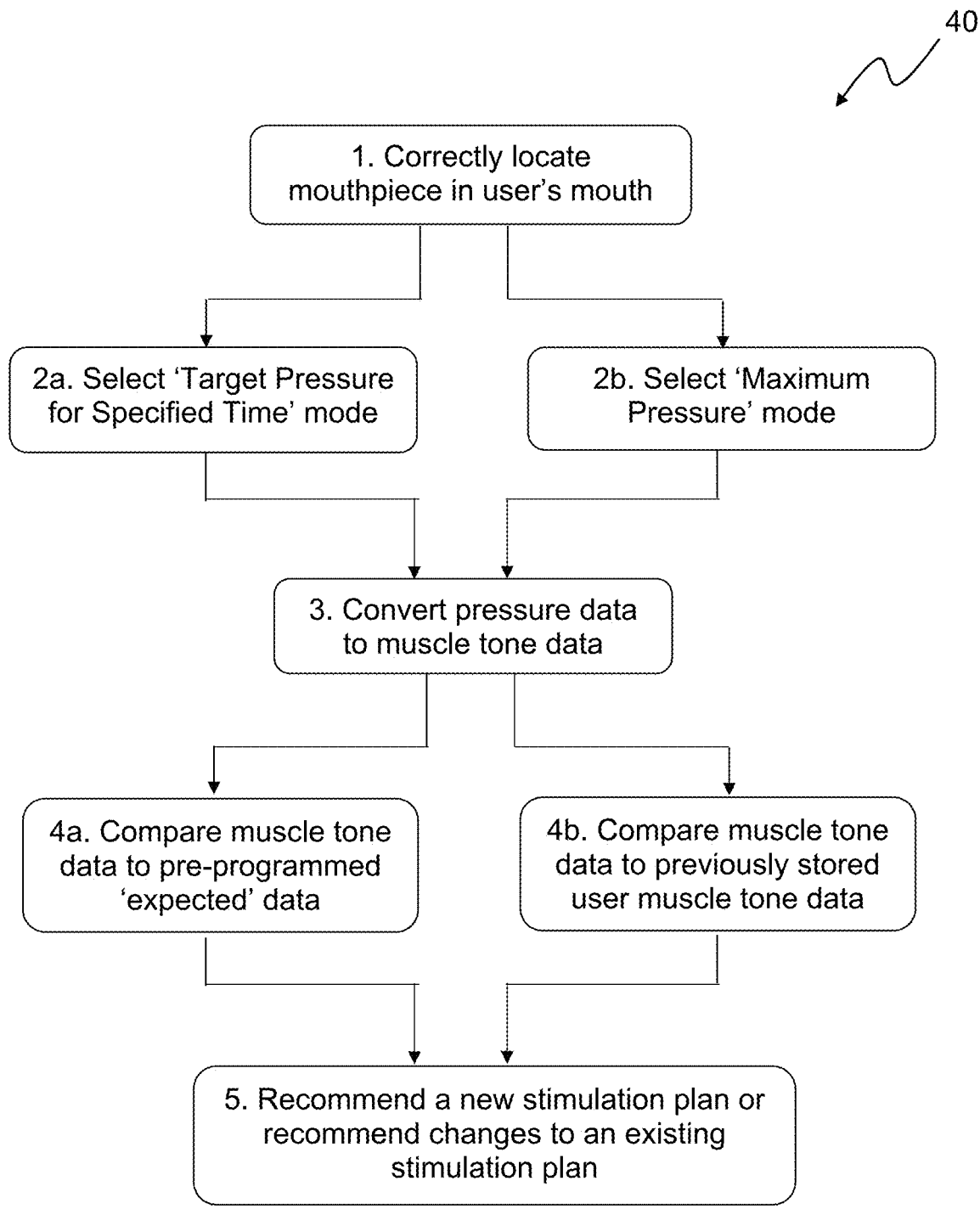
Figure 4B:
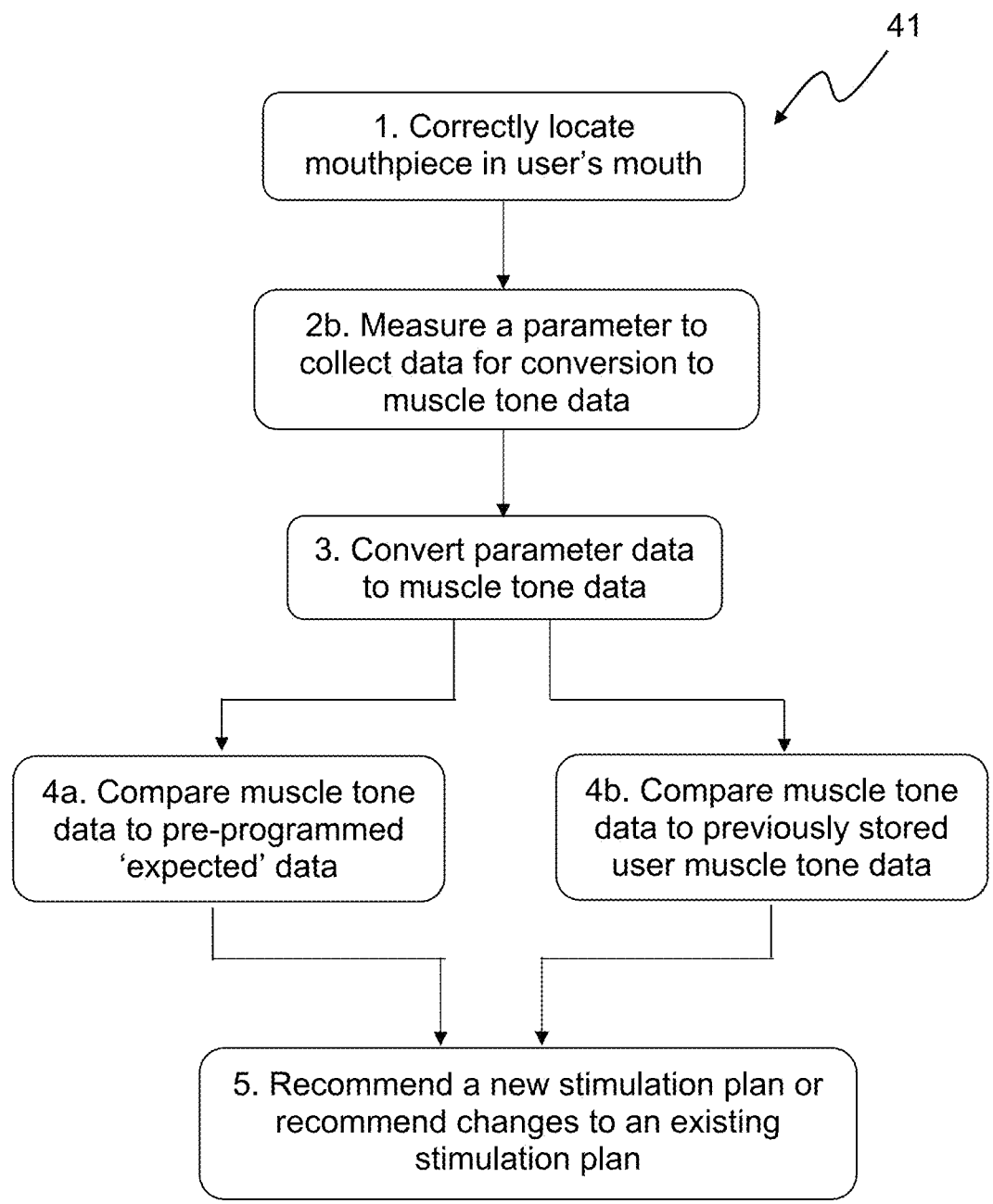
Figures 12A, 12B:
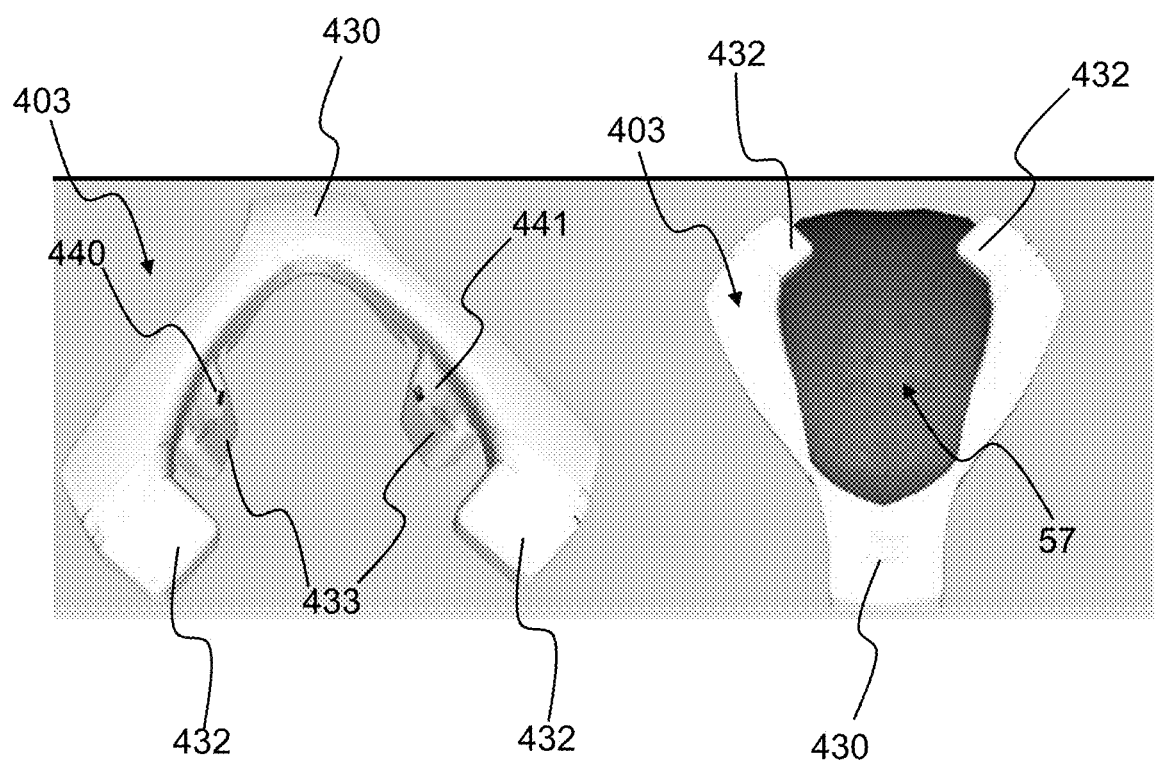

FIGS. 3A, 3B, and 3C are respectively perspective, plan, and side elevation views of a part of the apparatus according to a second embodiment of the invention;

FIGS. 3D and 3E show views of the apparatus of FIGS. 3A to 3C in use;

FIG. 4A is a flow diagram illustrating how the muscle tone data is recorded and used to inform a future treatment plan;

FIG. 4B is a flow diagram illustrating how the muscle tone data is recorded and used to inform a future treatment plan according to a further embodiment;

FIG. 5 is a schematic of a human mouth showing the palatoglossus and surface of the tongue;

FIG. 6 is a schematic illustrating the extrinsic tongue muscles of a human tongue;

FIG. 7 is a schematic illustrating the intrinsic tongue muscles of a human tongue;

FIG. 8 is another schematic of a human mouth showing the muscles of the palate;

FIG. 9 is a schematic illustrating further muscles of the palate;

FIGS. 10A and 10B is a mouthpiece, and the mouthpiece in use, for use in an apparatus according to a third embodiment of the invention;

FIGS. 11A and 11B is a mouthpiece, and the mouthpiece in use, for use in an apparatus according to a fourth embodiment of the invention; and FIGS. 12A and 12B is a mouthpiece, and the mouthpiece in use, for use in an apparatus according to a fifth embodiment of the invention.

Figure 1:
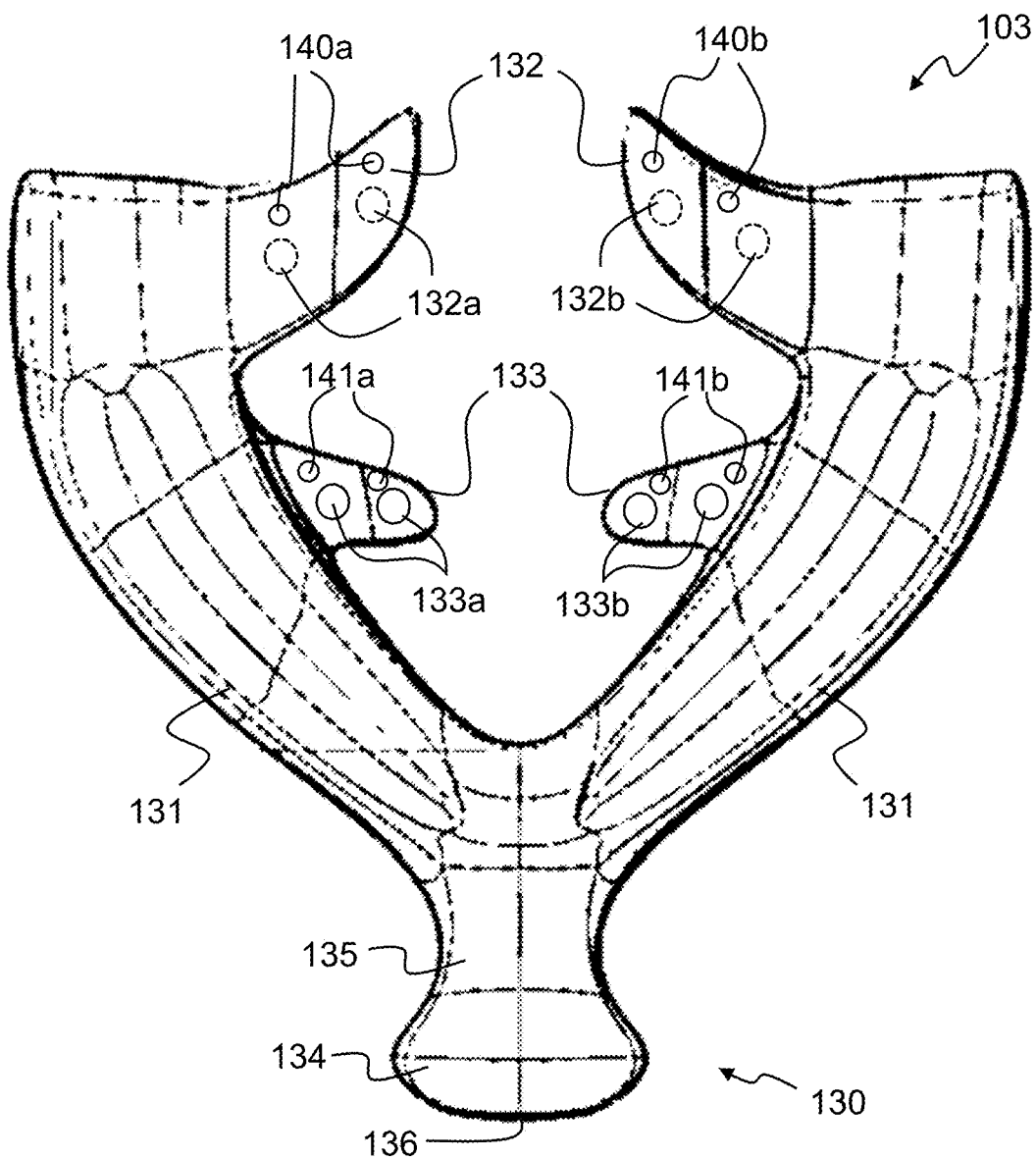
FIG. 1 is a plan view of a part of the apparatus according to an embodiment of the invention.
Figure 2:
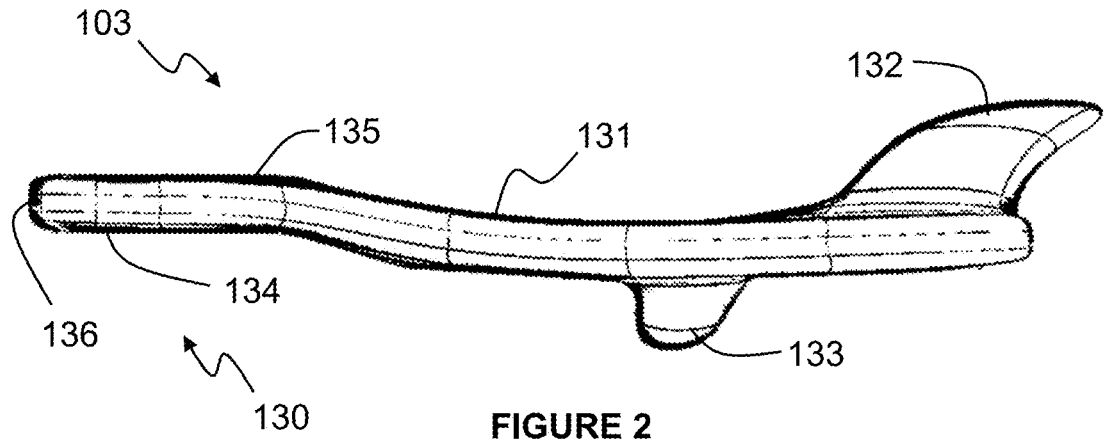
FIG. 2 is a side elevation of the of FIG. 1.

Referring now to FIGS. 1 and 2, there is a shown a component of the apparatus according to a first embodiment of the invention. The FIGS. 1 and 2 show a mouthpiece 103 which includes a gripping base 130 and a pair of curved arms 131 formed integrally with one end of the base 130 to form a horseshoe shape. Each of the arms has first and second contact flanges 132, 133 within are provided electrodes (132a, 132b; 133a, 133b).

The first contact flanges 132 extend inwardly toward one another from the free end of a respective one of the arms 131 and upwardly to form a curved shape for accommodating the dorsal tongue surface 57 (FIG. 6) of a tongue of a user (not shown). The second contact flanges 133 extend inwardly toward one another from an intermediate part of a respective one of the arms 131 and downwardly to form a curved shape for accommodating the sublingual tongue surface. As looked at from the side (FIG. 2), the electrode or electrodes 132a on the first contact flanges 132 will face downwardly whereas those electrodes 133a, 133b on the second contact flanges 133 will face upwardly. In this way, with the user's tongue located between the first 132 and second 133 contact flanges the electrodes 132a, 132b; 133a, 133b will apply an electrical field in a vertical direction and will specifically target the genioglossus muscle.

As shown in FIG. 1, the mouthpiece 103 further comprises measuring means for measuring the muscle tone of one or more oral muscles. In this embodiment, the measuring means comprise a first and a second set of pressure sensors 140a, 140b, and 141a, 141b respectively. The first set of pressure sensors 140a, 140b is located on the first contact flanges 132, such that each of the first contact flanges 132 comprises a pair of pressure sensors, 140a or 140b. The second set of pressure sensors 141a, 141b, is located on the second contact flanges 133, such that each of the second contact flanges 133 comprises a pair of pressure sensors, 141a or 141b. However, it is to be understood that at least some of the pressure sensors 140a, 140b or 141a, 141b may not be present, such that only one pressure sensor, or one set of pressure sensors is present, e.g. on the first contact flanges 132, or on the second contact flanges 133.

In alternative embodiments, the pressure sensors may be located at different locations on the mouthpiece 103, e.g. at an appropriate location on one of the arms.

The base 130 includes an enlarged end 134 joined to the arms 131 by a necked portion 135. The end surface of the enlarged end 134 includes an electrical connector 136 for connection with a source of power (not shown). The connector 136 may comprise a USB, microUSB, USB-C, FireWire®, Thuderbolt®, magnetic connectors or any other suitable type of wired connector. In other embodiments, the connector is replaced with a wireless connection means. In some embodiments, the mouthpiece incorporates a power source, such as a battery.

The mouthpiece 103 also includes electrical circuitry (not shown) connecting the respective series of electrodes 132a, 132b, 133a, 133b at each surface of each flange 132, 133, that is to say each of the upper and lower surfaces of each of the flanges 132, 133. The electrical circuitry (not shown) may also connect the respective sets of pressure sensors 140a, 140b, and 141a, 141b.

Each of these electrode series 132a, 132b; 133a, 133b is electrically isolated from the others by a shielding material, thereby enabling all surrounding muscles to be stimulated simultaneously or in any sequence required. The electrodes 132a, 132b; 133a, 133b cooperate with the outer surface of the flanges 132, 133 with which they are associated to form a substantially contiguous surface. In this embodiment, the mouthpiece 103 is formed of a food grade or a biocompatible grade plastic material, for example made from silicone plastics material. The electrodes 132a, 132b; 133a, 133b in this embodiment are preferably formed of metal, for example gold, silver or copper or composite material or any such alloy with an exposed surface.

In use, the mouthpiece 103 is placed in a patient's mouth and the tongue of the patient is received within the mouthpiece 103 such that the dorsal tongue surface 57 is in contact with the first contact flanges 132 and the sublingual tongue surface is in contact with the second contact flanges 133. It will be appreciated by those skilled in the art that the first flanges 132 will contact a rearward or posterior portion of the dorsal tongue surface 57 and the second flanges 133 will contact a frontward or anterior portion of the sublingual tongue surface. With the patient's mouth closed, the flanges 132, 133 are also able to contact and stimulate adjacent muscles on the other side of the tongue, for example the palate muscles.

During a stimulation session, the mouthpiece 103 enables the muscles to be stimulated, for example on both sides of the tongue simultaneously. It will be appreciated that with this design, the muscles based in and around the tongue may be stimulated, including those in hard and soft palate areas.

Referring now to FIGS. 3A, 3B, and 3C, there is shown a mouthpiece 103' according to a second embodiment of the invention. The mouthpiece 103' is similar to that shown in FIGS. 1 and 2 (and uses the same numerals to indicate the equivalent components but distinguished by a prime (') and is shown in FIGS. 3A, 3B, and 3C. The mouthpiece 103' has a gripping base 130' which has an extended and depending portion 135' which extends over a user's bottom lip (see FIG. 3D).

The terminal portion of the depending portion 130' has an interface 136' for engaging with a control and/or power unit (see FIGS. 3D and 3E) which is arranged to provide the power to the electrodes 132a', 132b', 133a', 133b' of the mouthpiece 103' and, optionally, to further optional electrodes. It is noted that the electrodes 132a', 132b', 133a', 133b' of the mouthpiece 103' are shown as single pads, although they could be multiple pads or contact points. We prefer a single pad as it provides a large surface area. The electrodes 132a', 132b', 133a', 133b' of the mouthpiece 103' protrude proud of the adjacent portions of the associated flanges 132', 133' to facilitate a good connection with the facing portion of the user's tongue.

In this embodiment, the measuring means comprise four single pressure sensors 140a', 140b', and 141a', 141b'. Each flange of the first contact flanges 132' comprises a single pressure sensor; either 140a' or 140b. Each flange of the second contact flanges 133' comprises a single pressure sensor; either 141a' (not shown in FIG. 3A) or 141b'. The pressure sensors 140a', 140b', and 141a', 141b' may be located on or under the electrodes 132a', 132b', 133a', 133b'. One or more of the pressure sensors 140a', 140b', and 141a', 141b' may be absent.

As shown in FIGS. 3D and 3E, the device 103' interfaces with a controller or control unit 150 via connection 136'. The controller or control unit 150 may also be connected to optional further electrodes 152a, 152b for stimulating muscles in the floor of the user's mouth by attachment to the external surface of the floor of the user's mouth F.

In order to train the muscles of the mouth, the control unit 150 is programmed (or a pre-programmed program is selected) and the mouthpiece 103' and optional electrodes 152a, 152b are connected to the control unit 150 to deliver electrical stimulation to various muscles according to a stimulation plan. Once the program has started, the control unit 150 will energise the electrodes 132a', 132b', 133a', 133b' (and optionally 152a, 152b) according to the required or desired stimulation plan or profile to apply the electrical stimulation to the muscles.

The control unit 150 may comprise batteries and logic and control circuitry (not shown) to control the application of electric currents to the various electrodes.

At certain times during delivery of the stimulation plan, or at a convenient time after or before commencement of a stimulation plan a test mode may be selected or activated. During the test mode the user will use the mouthpiece 103, 103' to determine the muscle tone of the tongue of the user.

The control unit 150 is programmed or programmable to measure the tone of one or more oral muscles of the user. In use, the appropriate program to measure the tone of one or more oral muscles may be selected to provide the user with instructions regarding the measurement of the muscle tone of the tongue of the user, for example by application of pressure by one or more oral muscles to a location on the mouthpiece comprising one or more pressure sensors, e.g. the pressure sensors 140a', 140b', 141a', 141b' or by exerting pressure over a certain time period, or measuring how exerted pressure changes over a certain time period.

Referring now to FIG. 4A, there is shown a flow diagram 40 illustrating how tongue muscle tone data may be recorded using the apparatus (e.g. apparatus comprising the mouthpieces 103, 103' shown in FIGS. 1 to 3) and system of the invention, and how the data may be used to inform a future stimulation plan, according to embodiments of the invention. The flow diagram comprises the following steps:

Step 1: Correctly Locate Mouthpiece in User's Mouth.

Before, after, during or instead of a stimulation session, the user may locate the mouthpiece, e.g. mouthpiece 103, 103', inside their mouth in the same fashion as is described for use during a stimulation session.

Step 2a: Select 'Target Pressure for Specified Time' Mode.

The user may select the program 'Target Pressure for Specified Time', for example, using the control unit 150 and/or a user interface (for example a computer software program operably connected to the controller 150). In the program 'Target Pressure for Specified Time', the user is required to apply a pressure specified by the program using their tongue muscles to the pressure sensors, for example pressure sensors 140a', 140b', 141a', 141b' on one of either the first contact flanges 132, 132' or the second contact flanges 133, 133'. Once the program is initiated by the user or the user interface, the control unit 150 or the user interface may issue instructions to the patient on the length of time required, and whether enough pressure (or whether too much pressure) is being applied. The control unit 150 or the user interface may issue instructions on when to cease applying pressure, when appropriate measurements have been taken from the pressure sensors.

Step 2b: Select 'Maximum Pressure' Mode.

As an alternative to Step 2a, the user may select the program 'Maximum Pressure', for example, using the control unit or user interface. In the program 'Maximum Pressure', the user is required to apply the maximum pressure that they are able to using their tongue muscles to the pressure sensors, for example pressure sensors 140a', 140b', 141a', 141b' on one of either the first contact flanges 132, 132' or the second contact flanges 133, 133'. Once the program is initiated by the user or the user interface, the control unit 150 or the user interface may issue instructions to the patient on when to cease applying pressure, when appropriate measurements have been taken from the pressure sensors.

Step 3: Convert Pressure Data to Muscle Tone Data.

The system may comprise a memory means on which is stored a database for the conversion of data from the pressure sensors into muscle tone data, and a processor, operably connected to the pressure sensors of the mouthpiece 103, 103' and to the memory means. In Step 3, the system is configured to determine the muscle tone of the tongue muscles of the user, by comparing the data from the pressure sensors with the data within the database of the memory means, using the processing means. In this way, the user is provided with a user readable or user interpretable value or output corresponding to the muscle tone of their tongue muscles.

Step 4a: Compare Muscle Tone Data to Pre-programmed 'Healthy' Data

Optionally, the system may perform Step 4a, which enables a comparison between pre-programmed 'expected' data, i.e. the expected muscle tone data from a user who has undergone the stimulation plan, and the user's muscle tone data from Step 3a or Step 3b.

Step 4b: Compare Muscle Tone Data to Previously Stored User Muscle Tone Data

Optionally, the system may perform Step 4b, in which muscle tone data previously collected from the user, e.g. at an earlier date or point in time or an earlier stage in a stimulation plan, is compared with the data collected in Step 2a, or Step 2b, and converted in Step 3.

Step 5: Recommend a new Stimulation Plan or Recommend Changes to an Existing Stimulation Plan Optionally, the system may be programmed or programmable to be able to make a recommendation of a new stimulation plan, e.g. for a new user, or for a user who has reached the end of their stimulation plan. Alternatively, the system may be programmed or programmable to be able to make a recommendation of changes to an existing stimulation plan.

If the device 103, 103' is used before any stimulation sessions it may be used to determine or establish a base point from which stimulation can begin. For example, when the user uses the device 103. 103' for the first time, 'Test Mode' may be selected (or may automatically select and the user is instructed to determine tongue muscle tone, for example by applying a maximum force to the sensor and/or by applying a force for a period of time. The device 103, 103' can measure the force parameters of the tongue and, via an interface (e.g. a computer software program held on a computing device operable connected to the system, for example via controller 150), compare those force parameters with a database of such force parameters to determine the risk of SDB, for example the likely risk of snoring versus the likely risk of OSA. Other data, for example one or more of age, sex, weight, height, BMI or other indicators may also be input to help with the risk determination. Once a risk profile has been established, a stimulation plan will be developed specific to the inputs.

The user will then use the device 103, 103' according to the stimulation plan, with the requisite stimulation sessions. For example, the stimulation sessions may comprise a daily routine of 20-minute sessions for two weeks, with energisation of the electrodes according to stimulation parameters (current, pulse width, pulse duration, frequency, amplitude) preferably during an awake state.

At the end of the stimulation plan the system may automatically activate (or a user may activate) a Test Mode to determine the efficacy of the stimulation plan by measuring tongue muscle tone. A comparison may then be completed to assess progress (i.e. changes to tongue muscle tone) against expected or predicted tongue muscle tone. A subsequent stimulation plan may then be developed according to the comparison. The subsequent stimulation plan may be the same or different as the first stimulation plan depending upon the results of the comparison.

The changes to an existing stimulation plan may include changes to parameters of the stimulation sessions of a stimulation plan including the intensity, frequency, and pulse duration of electric current being supplied to one or more electrodes of the apparatus, and/or the length of one or more of the stimulation sessions. In this way, the user is able to use the system of the invention to inform them of future stimulation plans, or changes that should be made to existing or ongoing stimulation plans.

Referring now to FIG. 4B, there is shown a flow diagram 41 illustrating how tongue muscle tone data may be recorded using the apparatus (e.g. apparatus comprising the mouthpieces 203, 303, 403 shown in FIGS. 10A, 11A, 12A) and system of the invention, and how the data may be used to inform a future stimulation plan, according to a further embodiment of the invention. The flow diagram comprises the following steps:

Step 1: Correctly Locate Mouthpiece in User'S Mouth.

Before, after, during or instead of a stimulation session, the user may locate the mouthpiece, e.g. mouthpiece 203, 303, 403, inside their mouth in the same fashion as is described for use during a stimulation session.

Step 2: Measure a Parameter to Collect Data for Conversion to Muscle Tone Data.

If the mouthpiece 203 is in use, then the user may select the program 'Measure mechanomyogram (MMG)'.

Alternatively, if the mouthpiece 303 or 403 is in use, then the user may select the program 'Measure peripheral capillary oxygen saturation ($SpO_2$)'.

This step may be performed, for example, using the control unit 150 and/or a user interface (for example a computer software program operably connected to the controller 150). Advantageously, the user does not need to actively participate during this measurement.

The control unit 150 or the user interface may issue instructions for the user to maintain their tongue in a specific position until appropriate measurements have been taken from the sensors of the mouthpiece, e.g. 203, 303, or 403.

Step 3: Convert Pressure Data to Muscle Tone Data.

The system may comprise a memory means on which is stored a database for the conversion of data from the sensors of mouthpieces 203, 303, or 403 into muscle tone data, and a processor, operably connected to said sensors of the mouthpiece 203, 303, 403 and to the memory means. In Step 3, the system is configured to determine the muscle tone of the tongue muscles of the user, by comparing the data from the sensors with the data within the database of the memory means, using the processing means. In this way, the user is provided with a user readable or user interpretable value or output corresponding to the muscle tone of their tongue muscles.

Step 4a, Step 4b, and Step 5 may be performed in the same manner as described for FIG. 4A.

In the methodologies above, impedance sensors may be used in addition to or as alternatives to the measurement techniques mentioned. The impedance measurements may be used to produce an image to visualise the status of the tongue muscle.

Turning now to FIGS. 5 to 9, there is shown various tongue and palate muscles. Features of the mouth shown in FIGS. 5 to 7 illustrate more clearly the tongue muscles, wherein there is shown the pharyngopalatine arch 51, palatine tonsil 52, palatoglossus 53, buccinator 54, valate papillae 55, fungiform papillae 56, dorsal tongue surface 57, styloglossus 58, hyoglossus 59, mandible bone 60, genioglossus 61, longitudinal, transverse and vertical intrinsic muscles 62, 63, 64 and geniohyoid 65.

It is well established that the tone of the genioglossus muscle 61 most affects the collapsibility of the tongue as it is the biggest of the extrinsic muscle and responsible for pulling the tongue forward and increasing the airway opening in the throat. The tone of intrinsic surface muscles, such as the longitudinal and transverse intrinsic muscles 62, 63, also contribute to the reduction of the collapsibility of the airway.

Features of the mouth shown in FIGS. 8 and 9 illustrate more clearly the palate muscles, wherein there is shown the dental arch 66, premaxilla 67, incisive foramen 68, palatine process of maxilla 69, palatine bone 70, posterior nasal spine 71, palatine foramen 72, hamulus 73, tensor palatini muscle 74, levator veli palatini muscle 75, tensor veli palatini muscle 76, uvular muscle 77 and palatopharyngeus muscle 78.

To a varying degree, the constrictor and dilator muscles of the palate also contribute to snoring and sleep apnoea. The aim of the treatment is to dilate the throat, hence electrical stimulation is directed at the dilatory palate muscles in the midline, such as the uvular muscle 77, the levator veli palatini muscle 75 and the palatopharyngeus muscle 78.

In use, the mouthpiece 103' is applied to the dorsal tongue surface 57 and/or the sublingual surface and current, for example biphasic currents are applied, each of which may be configured with a first set of parameters including intensity, frequency and pulse duration. The parameters are selected to provide maximal contraction of these muscles in the user and the treatment is carried out for a period of 20 minutes.

The intensity, frequency and pulse duration may then be adjusted and the mouthpiece 103' is applied to the underside of the tongue and/or the dorsal surface 57. The two currents, for example the two biphasic currents, now having a second set of parameters, are applied and transmitted trans mucosally to stimulate the genioglossus muscle 61. The second set of parameters are selected to provide maximal contraction of the user's genioglossus muscle 61 and the treatment is carried out for a period of, say, up to 3 hours, for example 20 to 30 minutes.

The application of currents, e.g. biphasic currents, according to the parameters described above stimulate the aforementioned skeletal muscles. It is also believed that the application of this biphasic current to these skeletal muscles creates a further, sensory function, such as a vibratory sensation. Whilst not wishing to be bound by any theory, it is believed that this electrical and vibratory stimulation of the nerves provides feed back to the brain which further enhances the improvement in muscle tone. Specifically, it is believed that the effectiveness of this treatment is enhanced by multisensory integration within the nervous system.

By way of example, a treatment regime could involve a say six-week induction period during which each of the aforementioned muscle groups are stimulated for a period of 10 to 30 minutes, twice daily. The treatment regime, which is designed to build muscle tone, could then be followed by an ongoing maintenance regime involving 10 to 20 minute sessions once per day.

The apparatus comprising the mouthpiece 103' may be operable to adjust the current amplitude of a first current, e.g. first biphasic or monophasic current, from 0 to 100 mA. The apparatus may be operable to adjust the current amplitude of, for example, a second biphasic current from 0 to 100 mA. The apparatus may be operable to adjust the duration of the period during which the first current, e.g. biphasic current is supplied from 1 to 30 minutes. The apparatus may be operable to adjust the duration of the period during which the second current e.g. biphasic or monophasic current is supplied from 1 to 30 minutes.

A USB port or other interface may be provided and configured to enable the device 103, 103' to be connected to a personal computer (not shown) to program one or more characteristics of the first and second currents, e.g. biphasic or monophasic currents, independently. In an embodiment, the frequency of the first current, e.g. biphasic current, is set at a value between say 1 and 150 Hz, for example between 2 and 50 Hz, the second current, e.g. second monophasic current, is set at a value between 3 and 120 Hz and the pulse duration of each current, e.g. biphasic or monophasic current, may be set at a value between 200 and 700 μs. The personal computer, tablet, smartphone or other hand-held computing device (not shown) may also incorporate control software operable to override any, say, dials or buttons or other user interface on the control body. The software may be programmed to apply currents, e.g. biphasic or monophasic currents, having predetermined characteristics independent from one another, such as amplitudes, frequencies and pulse durations and for a predetermined period of time. Additionally or alternatively, the software may be programmed to run a measurement of the muscle tone of one or more oral muscles of the user, e.g. using a protocol as described in FIG. 4 and/or using impedance sensors to generate impedance information. It is further envisaged that the device 103, 103' could incorporate a memory on which is stored such predetermined characteristics, which may be modified by connecting a personal computer or so on (not shown) to the device 103, 103' via the USB port or other interface. In such embodiments, the dials may be omitted or configured to adjust the aforementioned characteristics from their pre-programmed values. In some embodiments, it is envisaged that more or less functionality is provided by manual dials, buttons and the like.

The above description discloses a 'Test Mode' in which the user applies a pressure to the device 103, 103'. It is also possible to cause the device 103, 103' to stimulate the tongue and then measure the response as a result of the stimulation signal. In this way the device 103, 103' is able to provide a quantitative 'signal-response' parameter which does not require a user to consciously apply a pressure to the sensors. Accordingly, the device 103, 103' is able to determine the stimulation plan. It is possible that both automatic determinations and 'user-actuated' determinations may be used in concert. The stimulation may cause the tongue to apply a pressure to the pressure sensor. Additionally or alternatively, a sensor may monitor how effectively an electrical stimulation signal is transmitted across the tongue. For example, a sensor and/or one or more electrodes on, say, the upper flanges 132, 132' may detect a signal transmitted from the lower flanges 133, 133' to determine impedance and/or tongue muscle tone. Additionally or alternatively, a sensor on say one of the upper flanges 132 may detect a signal transmitted from the other of the upper flange 132 to determine muscle tongue tone. Other combinations will be apparent to the skilled person. In an embodiment the sensor may be or may comprise one of the electrodes. For example, the electric circuitry may be able to determine how effectively a signal is transmitted from one electrode to another electrode. The transmittal and receipt of a signal may be used to determine the attenuation or other perturbation of the signal and thereby determine a parameter which can be compared to a database of stored or recorded data to provide an indication of tongue muscle tone.

Referring now to FIG. 10A, there is shown a mouthpiece 203 according to a third embodiment of the invention. The mouthpiece 203 is similar to that shown in FIGS. 1, 2, and 3A to 3C and has many of the same features which function in a like manner to that previously described. The mouthpiece 203 comprises a gripping base 230, a first set of contact flanges 232, a second set of contact flanges 233, a first set of electrodes (not shown), and a second set of electrodes (not shown). The first set of electrodes is located on the first set of contact flanges 232. The second set of electrodes is located on the second set of contact flanges 233 in a like manner to that described for the mouthpiece 103' of FIG. 3A.

In this embodiment, the measuring means comprises two sensors 240, 241 for use in detecting or recording a mechanomyogram (MMG) of one or more muscles. The sensors 240, 241 are located on the second set of contact flanges 233 adjacent the second set of electrodes (not shown) respectively.

Referring also to FIG. 10B, there is shown the mouthpiece 203 in use located adjacent the tongue of the user. The dorsal surface of the tongue 57 is labelled. It is shown that the sensors 240, 241 contact the underside of the tongue.

Each sensor 240, 241 in this embodiment is an analog silicon MEMS (microelectro-mechanical systems) microphone, for example, an AKU340® made by Akustica, Inc. of the Bosch Group (Gerlingen, Germany).

The mouthpiece 203 may be connected to a control unit (not shown), which is configured to determine changes in the muscle tone of the user. In use, the two sensors 240, 241 record sub-sonic frequencies produced by the skeletal muscles. It has been found that, during contraction of one or more tongue muscles, there is a change in mechanical vibrations produced by those muscles. The two sensors 240, 241 are configured to detect these changes. The resulting mechanomyogram (MMG) is usable to determine changes in the muscle fibre, which is indicative of the muscle tone of the tongue of the user.

Advantageously, this method is passive so the user does not need to actively interact with the mouthpiece in order for the device to determine the muscle tone of the tongue of the user. More advantageously, the sensors 240, 241 have a low power consumption in comparison to sensors that require active interaction of the user.

Referring now to FIG. 11A, there is shown a mouthpiece 303 according to a fourth embodiment of the invention. The mouthpiece 303 is similar to that shown in FIGS. 1, 2, 3A to 3C, and 10A and has many of the same features which function in a like manner to that previously described. The mouthpiece 303 comprises a gripping base 330, a first set of contact flanges 332, a second set of contact flanges 333, a first set of electrodes (not shown), and a second set of electrodes (not shown). The first set of electrodes is located on the first set of contact flanges 332. The second set of electrodes is located on the second set of contact flanges 333 in a like manner to that described for the mouthpiece 103' of FIG. 3A.

In this embodiment, the measuring means comprises two optical reflectance sensors 340, 341 for use in measuring the partial pressure of oxygen in the peripheral circulation ($SpO_2$). The sensors 340, 341 are located on the second set of contact flanges 333 adjacent the second set of electrodes (not shown) respectively.

Referring also to FIG. 11B, there is shown the mouthpiece 303 in use located adjacent the tongue of the user. The dorsal surface of the tongue 57 is labelled. It is shown that the sensors 340, 341 contact the underside of the tongue.

The mouthpiece 303 may be connected to a control unit (not shown), which is configured to determine changes in the muscle tone of the user. In use, the two sensors 340, 341 record the partial pressure of oxygen in the peripheral circulation ($SpO_2$) of one or more muscles in the tongue of the user. These measurements are usable to determine the increase in vascularity of the muscles, which in turn, may be used to determine muscle function, and specifically to determine the muscle tone of the tongue of the user.

Referring now to FIG. 12A, there is shown a mouthpiece 403 according to a fifth embodiment of the invention. The mouthpiece 403 is similar to that shown in FIGS. 1, 2, 3A to 3C, 10A, and 11A and has many of the same features which function in a like manner to that previously described. The mouthpiece 403 comprises a gripping base 430, a first set of contact flanges 432, a second set of contact flanges 433, a first set of electrodes (not shown), and a second set of electrodes (not shown). The first set of electrodes is located on the first set of contact flanges 432. The second set of electrodes is located on the second set of contact flanges 433 in a like manner to that described for the mouthpiece 103' of FIG. 3A.

In this embodiment, the measuring means comprises two optical transmission sensors 440, 441 for use in measuring the partial pressure of oxygen in the peripheral circulation ($SpO_2$). The sensors 440, 441 are located on the second set of contact flanges 433 adjacent the second set of electrodes (not shown) respectively.

Referring also to FIG. 11B, there is shown the mouthpiece 403 in use located adjacent the tongue of the user. The dorsal surface of the tongue 57 is labelled. It is shown that the sensors 440, 441 contact the underside of the tongue.

The mouthpiece 303 may be connected to a control unit (not shown), which is configured to determine changes in the muscle tone of the user. In use, the two sensors 440, 441 record the partial pressure of oxygen in the peripheral circulation ($SpO_2$) of one or more muscles in the tongue of the user. Wavelengths of approximately 810 nm are used to enable high cutaneous penetration. This wavelength can easily pass through the muscle tissue of the tongue. The difference in the optical transmission through the tongue muscle is usable to determine changes in the muscle tone and vascularity of the muscle of the user.

Advantageously, the sensors 440, 441 of this embodiment may be integrated into a system for providing feedback to the user on improvements to the muscle tone of their tongue.

It will be appreciated by those skilled in the art that several variations to the aforementioned embodiments are envisaged without departing from the scope of the invention. For example, the mouthpiece 103, 103' may take any suitable form, but is preferably designed to enable the electrical stimulation to be applied to the appropriate muscles as described above. The output of the control body may be varied by changing dials on the body itself or it may be altered by interfacing the control unit (not shown) with, for example software, such as an APP held on a mobile device, such as a personal computer, smart phone or tablet. The software may be programmed to apply desired or required currents, for example biphasic currents, having predetermined characteristics (current, duration, frequency) independent from one another, such as amplitudes, frequencies and pulse durations and for a predetermined period of time. It is further envisaged that the apparatus could incorporate a memory on which is stored such predetermined characteristics, which may be modified by connecting a personal computer (not shown) to the apparatus via a USB port or other interface connection. Other interface connections include wired and wireless connections, for example Bluetooth®, Wi-Fi and so on. Other sensors may be deployed which allow for the measurement of muscle tone.

As will be appreciated, the device 103, 103' can be used as a diagnostic tool to determine the likelihood of SDB (e.g. snoring or OSA) by using the device 103, 103' prior to using the device for a stimulation session.

It will also be appreciated by those skilled in the art that any number of combinations of the aforementioned features and/or those shown in the appended drawings provide clear advantages over the prior art and are therefore within the scope of the invention described herein.

The invention claimed is:

1. An apparatus for applying an electrical stimulation to the mouth of an awake user to train the muscles of the mouth, the apparatus comprising:

a device comprising one or more electrodes for applying electrical stimulation to train one or more muscles of the mouth of the user during an awake state, the electrical stimulation configured to increase muscle tone of the one or more muscles of the mouth during sleep;

a pressure sensor for determining the awake muscle tone of the tongue of the user;

a controller configured to provide output of the user while the user is operating the apparatus and alter the electrical stimulation based on an input from the user; and a switch operable to switch the device from a stimulation mode to a test mode and vice versa, wherein in the test mode the controller is configured to guide the user to apply tongue pressure to the pressure sensor using a user interface, further wherein the controller determines muscle tone in the user based on the applied tongue pressure.

2. The apparatus according to claim 1, wherein the device comprises a mouthpiece for locating in a user's mouth.

3. The apparatus according to claim 1, wherein the device comprises a pair of arms connected together at a connecting portion and extending away from one another.

4. The apparatus according to claim 3, wherein the sensor is located on the arms.

5. The apparatus according to claim 1, wherein the device comprises flanges for overlying at least a portion of the dorsal or sublingual surface of the user's tongue.

6. The apparatus according to claim 5, wherein the sensor is located on the flanges.

7. The apparatus according to claim 1, wherein the switch is configured to be controlled by the awake user.

8. The apparatus according to claim 1, wherein the sensor is selected from one or more of a pressure sensor, a microphone, an optical transmission sensor, an impedance sensor or an optical reflectance sensor.

9. The apparatus according to claim 1, wherein the sensor comprises an electrical signal sensor.

10. The apparatus according to claim 1, further comprising memory to hold data relating to one or both of the electrical stimulation which has been applied to said one or more muscles and/or data relating to the output of the sensor.

11. The apparatus according to claim 1, further comprising a processor to process data relating to one or both of the electrical stimulation which has been applied to said one or more muscles and/or data relating to the output of the sensor.

12. The apparatus according to claim 11, wherein the processor is operable to control the controller based on data processed by the processor.

13. The apparatus according to claim 1, wherein the sensor is operable to provide data when in the test mode and not operable to provide data when in the stimulation mode.

14. A method of providing a stimulation plan to train one or more muscles of the mouth in an awake user, the method comprising;

locating a mouthpiece having one or more electrodes in the mouth of the awake user;

guiding the awake user to apply tongue pressure to a pressure sensor, wherein the user is guided by a user interface when the mouthpiece is in a test mode;

determining the muscle tone of the tongue of the mouth of the awake user based on the pressure applied by the tongue to the pressure sensor;

generating a stimulation plan to stimulate the one or more muscles of the mouth of the user during an awake state, the stimulation plan generated based on the determined muscle tone; and switching the mouthpiece from the test mode to a stimulation mode to activate the stimulation plan in the awake user during the awake state, the stimulation plan configured to increase resting muscle tone of the one or more muscles of the mouth.

15. The method according to claim 14, further comprising providing user-related data, wherein the user-related data is one or more of age, weight, height, body mass index (BMI).

16. A method of altering a stimulation plan to train one or more muscles of the mouth in an awake user, the method comprising;

providing a stimulation plan for electrically stimulating one or more muscles of a tongue of the user while the user is in an awake state;

locating a mouthpiece in the mouth of the awake user;

guiding the awake user, with a user interface, to apply tongue pressure to a pressure sensor when the mouthpiece is in a test mode;

determining the muscle tone of one or more muscles of the tongue of the awake user based on the pressure applied by the tongue to the pressure sensor;

adjusting the stimulation plan according to the determined muscle tone of the awake user; and switching the mouthpiece from the test mode to a stimulation mode to activate the stimulation plan for the awake user while the user is in the awake state.

17. The method according to claim 16, wherein adjusting the stimulation plan comprises comparing the determined muscle tone to a desired or expected muscle tone and adjusting the stimulation plan accordingly.

18. The method according to claim 16, wherein switching the mouthpiece from the test mode to a stimulation mode comprises switching by the awake user while the user is in the awake state.

* * * * *